(12) United States Patent
Matsuoka et al.

(10) Patent No.: US 7,943,748 B2
(45) Date of Patent: May 17, 2011

(54) GLUCITOL DERIVATIVE, PRODRUG THEREOF AND SALT THEREOF, AND THERAPEUTIC AGENT CONTAINING THE SAME FOR DIABETES

(75) Inventors: Hiroharu Matsuoka, Shizuoka (JP); Tsutomu Sato, Shizuoka (JP); Masahiro Nishimoto, Shizuoka (JP); Yasuhara Kato, Shizuoka (JP); Masahiro Sakaitani, Shizuoka (JP); Sang-Hak Lee, Kyunggi-do (KR)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1031 days.

(21) Appl. No.: 11/658,765

(22) PCT Filed: Jul. 27, 2005

(86) PCT No.: PCT/JP2005/013716
§ 371 (c)(1),
(2), (4) Date: Jan. 29, 2007

(87) PCT Pub. No.: WO2006/011502
PCT Pub. Date: Feb. 2, 2006

(65) Prior Publication Data
US 2008/0319047 A1 Dec. 25, 2008

(30) Foreign Application Priority Data

Jul. 27, 2004 (JP) .................................. 2004-218895
Nov. 29, 2004 (JP) .................................. 2004-343942

(51) Int. Cl.
C07H 1/00 (2006.01)
A01N 43/04 (2006.01)
A61K 31/70 (2006.01)

(52) U.S. Cl. ........................................ 536/1.11; 514/23

(58) Field of Classification Search .................. None
See application file for complete search history.

(56) References Cited

U.S. PATENT DOCUMENTS

| | | | |
|---|---|---|---|
| 6,048,842 A | 4/2000 | Tsujihara et al. | |
| 6,414,126 B1 | 7/2002 | Ellsworth et al. | |
| 2001/0041674 A1 | 11/2001 | Tomiyama et al. | |
| 2002/0137903 A1 | 9/2002 | Ellsworth et al. | |
| 2003/0114390 A1 | 6/2003 | Washburn et al. | |
| 2005/0233988 A1 | 10/2005 | Nomura et al. | |

FOREIGN PATENT DOCUMENTS

| | | |
|---|---|---|
| CA | 2493391 A1 | 1/2004 |
| CA | 2508024 A1 | 6/2004 |
| CA | 2508226 A1 | 6/2004 |
| EP | 0598359 A1 | 5/1994 |
| EP | 0684254 A1 | 11/1995 |
| EP | 1213296 A1 | 6/2002 |
| EP | 1270584 A1 | 1/2003 |
| EP | 1367060 A1 | 3/2003 |
| EP | 1329456 A1 | 7/2003 |
| EP | 1338603 A1 | 8/2003 |
| EP | 1344780 A1 | 9/2003 |
| EP | 1354888 A1 | 10/2003 |
| EP | 1364957 A1 | 11/2003 |
| EP | 1364958 A1 | 11/2003 |
| EP | 1389621 A1 | 2/2004 |
| EP | 1400529 A1 | 3/2004 |
| EP | 1405859 A1 | 4/2004 |
| EP | 1500403 A1 | 1/2005 |
| EP | 1528066 A1 | 4/2005 |
| EP | 1553094 A1 | 7/2005 |
| EP | 1577317 A1 | 9/2005 |
| JP | H08027006 A | 1/1996 |
| JP | H09124684 A | 5/1997 |
| JP | H09124685 A | 5/1997 |
| JP | H09188625 A | 7/1997 |
| JP | 2000080041 A | 3/2000 |
| JP | 2001288178 A | 10/2001 |

(Continued)

OTHER PUBLICATIONS

Devendra et al. BMJ vol. 328, Mar. 27, 2004, pp. 750-754.* Atkinson et al. The Lancet, vol. 358, Jul. 21, 2001, pp. 221-229.*
Link, J. et al., "A Method for Preparing C-Glucosides Related to Phlorizin", Tetrahedron Letter, vol. 13, No. 14, pp. 9213-9217, (2004).
Koji, O. et al., "Pyrazole-0-Glucosides as Novel Na+-Glucose Cotransporter (SGLT) Inhibitors", Bioorganic & Medicinal Chemistry Letter, vol. 13, pp. 2269-2272, (2003).

(Continued)

Primary Examiner — Anna Jiang
Assistant Examiner — Layla Bland
(74) Attorney, Agent, or Firm — Browdy and Neimark, PLLC

(57) ABSTRACT

The invention provides a glucitol derivative having the function of reducing a blood sugar level and having preferable properties required of medicines, such as long-lasting drug activity; and a medicinal composition for use in the prevention or treatment of diseases attributable to hyperglycemia, such as diabetes, complications of diabetes, and obesity. The derivative is a compound represented by the formula (I):

[Formula 1]

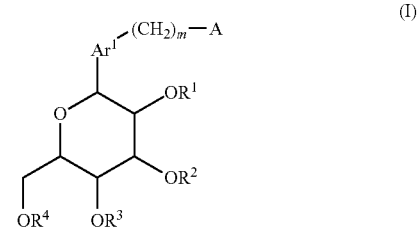

wherein m is an integer selected among 1-3; $R^1$ to $R^4$ each independently is optionally substituted alkyl, etc.; Ar1 is optionally substituted naphthyl; and A is optionally substituted heteroaryl, a prodrug of the compound, or a pharmaceutically acceptable salt of either. Also provided are a medicine, a medicinal composition, and the like each containing the compound.

10 Claims, No Drawings

FOREIGN PATENT DOCUMENTS

| | | | |
|---|---|---|---|
| JP | 2003012686 A | 1/2003 |
| WO | WO 97/31006 A1 | 8/1997 |
| WO | 0127128 A1 | 4/2001 |
| WO | 0174834 A1 | 10/2001 |
| WO | 0174835 A1 | 10/2001 |
| WO | WO 02/083066 A2 | 10/2002 |
| WO | 03011880 A1 | 2/2003 |
| WO | 03020737 A1 | 3/2003 |
| WO | 03099836 A1 | 12/2003 |
| WO | WO 2004/013118 A1 | 2/2004 |
| WO | WO 2004/080990 A1 | 2/2005 |
| WO | WO 2005-012326 A1 | 2/2005 |
| WO | WO 2005012326 A1 * | 2/2005 |

OTHER PUBLICATIONS

Hongu, M. et al., "Na+-Glucose Cotransporter Inhibitors as Anitdiabetic Agents. III. 1) Synthesis and Pharmacological Properties of 4'-Dehydroxyphlorizin Derivatives Modified at the OH Groups of the Moiety", Chem. Pharm. Bull., vol. 46, No. 10, pp. 1545-1555, (1998).

Hongu, M. et al., "Na+-Glucose Cotransporter Inhibitors as Anitdiabetic Agents. II. 1) Synthesis and Structure Activity Relationships of 4'-Dehydroxyphlorizin Derivatives", Chem. Pharm. Bull., vol. 46, No. 1, pp. 22-23, (1998).

Tsujihara, K. et al., "Na+-Glucose Cotransporter Inhibitors as Anitdiabetics I. Synthesis and Pharmacological Properties of 4'-Dehydroxyphlorizin Derivatives Based on A New Concept", Chem. Pharm. Bull., vol. 44, No. 6, pp. 1174-1180, (1996).

Tsujihara, K. et al., "Na+-Glucose Cotransporter (SGLT) Inhibitors as Anitdiabetic Agents 4. Synthesis and Pharmacological Properties of 4'-Dehydroxyphlorizin Derivatives Based on Substituted Ring on the B Ring", J. Med. Chem., vol. 42, pp. 5311-5324, (1999).

Kanai, et al., "The Human Kidney Low Affinity NA+/Glucose Cotransporter SGLT2: Delineation of the Major Renal Reabsorptive Mechanism for D-Glucose," J. Clin. Invest. 93:397-404 (1994).

* cited by examiner

GLUCITOL DERIVATIVE, PRODRUG THEREOF AND SALT THEREOF, AND THERAPEUTIC AGENT CONTAINING THE SAME FOR DIABETES

TECHNICAL FIELD

The present invention relates to glucitol derivatives, their prodrugs and their pharmaceutically acceptable salts which are useful as drugs. Particularly, the present invention relates to glucitol derivatives, their prodrugs and their salts which are useful as prophylactic or therapeutic agents for diabetes such as insulin dependent diabetes (type I diabetes) and insulin independent diabetes (type II diabetes), diabetic complications and diseases such as obesity caused by hyperglycemia by inhibiting $Na^+$-glucose co-transporter 2 (SGLT2).

BACKGROUND ART

In recent years, the number of diabetic patients has increased due to the westernized dietary habits and chronic lack of exercise and the like. In diabetic patients, the insulin secretion and insulin sensitivity are both reduced due to chronic hyperglycemia and this invites further rise in blood sugar levels to deteriorate the condition of the disease. As the therapeutic agents for diabetes, biguanide drugs, sulfonylurea drugs, glycosidase inhibitor drugs, insulin resistance improving agents and the like have been used. However, as the side effects associated with these agents, lactic acidosis is reported for the bigunide drugs, and hypoglycemia is reported for sulfonylurea drugs and diarrhea is reported for the glycosidase inhibitors, and therefore the actual condition is that the development of therapeutic agents for diabetes having a new mechanism of action different from that of these drugs is earnestly desired.

It was reported (see Non-patent Document 1) that phlorizin, a natural-occurring glucose derivative, inhibits reabsorption of excess glucose in the kidney by inhibiting sodium-dependent glucose co-transporter 2 (SGLT2) present in the S1 site of renal proximal convoluted tubule and promotes glucose excretion to exhibit lowering of blood sugar levels, and since then the study of therapeutic agents for diabetes based on the SGLT2 inhibition has been eagerly conducted.

For example, in Japanese Patent Publication 2000-080041 A (Patent Document 1), International Publication Nos. WO01/068660 (Patent Document 2), WO04/007517 (Patent Document 3) and the like, compounds used as SGLT2 inhibitors are reported. However, it is regarded as a problem that on oral administration, these compounds are easily hydrolyzed by glucosidase present in the small intestine or the like, and their pharmacological action quickly disappears. In the case of phlorizin, it is reported that phloretin, the aglycon of the phlorizin, strongly inhibits a sugar transporter of the facilitated diffusion type. For example, when phlorizin is intravenously administered to a rat, an adverse effect of reducing the intracerebral glucose concentration is reported (refer to, for example, Non-patent Document 2).

Then, in order to prevent such decomposition and improve absorption efficiency, some attempt to convert such compounds to prodrugs thereof has been carried out. When a prodrug is administered, it is desired that the prodrug be appropriately metabolized in or near a target organ to change into an active compound. However, since various metabolic enzymes are present in a living body and individual variability is considerable, in many cases, it is difficult to provide an action of a prodrug stably. Further, the conversion of the glycoside bond of the compound to a carbon-carbon bond has been attempted (refer to Patent Documents 4 to 8). However, further improvement of the properties as a drug, including activity, metabolic stability and the like are demanded.

Patent Document 1: Japanese Patent Publication 2000-080041 A
Patent Document 2: International Publication No. WO01/068660 Pamphlet
Patent Document 3: International Publication No. WO04/007517 Pamphlet
Patent Document 4: US Patent Publication 2001/041674 A
Patent Document 5: US Patent Publication 2002/137903 A
Patent Document 6: International Publication No. WO01/027128 Pamphlet
Patent Document 7: International Publication No. WO02/083066 Pamphlet
Patent Document 8: International Publication No. WO04/013118 Pamphlet
Non-patent Document 1: J. Clin. Invest., 93, 397-404 (1994)
Non-patent Document 2: Stroke, 14, 388 (1983)

DISCLOSURE OF THE INVENTION

Problem to be Solved by the Invention

The object of the present invention is to provide glucitol derivatives having suitable properties as drugs. The object of the present invention is particularly to provide glucitol derivatives which have blood sugar level lowering action and furthermore have suitable properties as drugs such as prolonged effect, metabolic stability and safety. Furthermore, the object of the present invention is to provide pharmaceutical compositions which are used in the prophylaxis or therapy of diabetes such as insulin-dependent diabetes (type I diabetes) and insulin-independent diabetes (type II diabetes), diabetic complications and diseases such as obesity caused by hyperglycemia.

Means to Solve the Problem

As the result of strenuous investigations by the present inventors in order to achieve the above-described objects, the inventors found that the glucitol derivatives represented by formula (I) have excellent SGLT2 inhibition activity, and the present invention has been completed.

That is, according to one aspect of the present invention, there is provided a compound represented by formula (I)

[Formula 1]

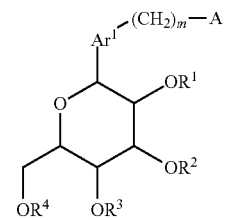

(I)

wherein
m is an integer selected from 1 to 3;
$R^1$, $R^2$, $R^3$ and $R^4$ are each independently selected from a hydrogen atom, a $C_1$-$C_6$ alkyl group which may be substituted with one or more Ra, a $C_7$-$C_{14}$ aralkyl group which may be substituted with one or more Rb, and —C(=O)Rx;

Rx is a $C_1$-$C_6$ alkyl group which may be substituted with one or more Ra, an aryl group which may be substituted with one or more Rb, a heteroaryl group which may be substituted with one or more Rb, a $C_1$-$C_6$ alkoxy group which may be substituted with one or more Ra, or —NReRf;

$Ar^1$ is a naphthyl group which may be substituted with one or more Rb;

A is a heteroaryl group which may be substituted with one or more Rb where the heteroaryl group may form a fused ring with an aromatic carbocycle or an aromatic heterocycle, provided that when A is a benzo-fused ring containing two or more rings, the group —$(CH_2)_m$— is linked on to a heterocycle in A;

Ra is each independently selected from a halogen atom, a hydroxy group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkoxycarbonyl group which may be substituted with one or more Rc, and a $C_1$-$C_6$ alkylcarbonyl group which may be substituted with one or more Rc;

Rb is each independently selected from a $C_1$-$C_6$ alkyl group which may be substituted with one or more Rc, a $C_3$-$C_8$ cycloalkyl group which may be substituted with one or more Rc, a $C_7$-$C_{14}$ aralkyl group which may be substituted with one or more Rd, a halogen atom, a hydroxy group, a cyano group, a nitro group, a carboxyl group, a $C_1$-$C_6$ alkoxycarbonyl group which may be substituted with one or more Rc, a $C_1$-$C_6$ alkoxy group which may be substituted with one or more Rc, an aryl group which may be substituted with one or more Rd, an aryloxy group which may be substituted with one or more Rd, a heteroaryl group which may be substituted with Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkylcarbonyl group which may be substituted with one or more Rc, a $C_1$-$C_3$ alkylenedioxy group, and a heterocyclyl group;

Rc is each independently selected from a halogen atom, a hydroxy group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamino group, and a di($C_1$-$C_6$ alkyl)amino group;

Rd is each independently selected from a $C_1$-$C_6$ alkyl group which may be substituted with one or more halogen atoms, a $C_7$-$C_{14}$ aralkyl group, a halogen atom, a hydroxy group, a cyano group, a nitro group, an amino group, a $C_1$-$C_6$ alkylamino group, and a di($C_1$-$C_6$alkyl) amino group;

Re is a hydrogen atom, a $C_1$-$C_6$ alkyl group which may be substituted with one or more Rc, an aryl group which may be substituted with one or more Rd, or a heteroaryl group which may be substituted with one or more Rd;

Rf is a hydrogen atom, or a $C_1$-$C_6$ alkyl group which may be substituted with one or more Rc;

Rg is a hydrogen atom, a $C_1$-$C_6$ alkyl group which may be substituted with Rc, a $C_1$-$C_6$ alkylcarbonyl group which may be substituted with one or more Rc, an aryl group which may be substituted with Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc; or Re and Rf, and Rf and Rg may form a 4- to 7-membered heterocycle together with the nitrogen atom to which they are bonded or a prodrug or a pharmaceutically acceptable salt thereof.

According to another aspect of the present invention, there is provided a compound represented by formula (Ia):

[Formula 2]

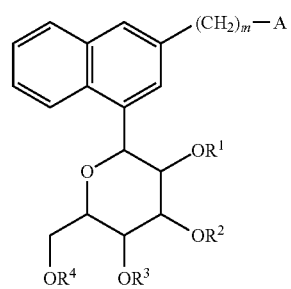

(Ia)

wherein A, $R^1$, $R^2$, $R^3$, $R^4$ and m are the same as above defined, or a prodrug or a pharmacologically acceptable salt thereof.

According to a further aspect of the present invention, there is provided a compound represented by formula (Ib):

[Formula 3]

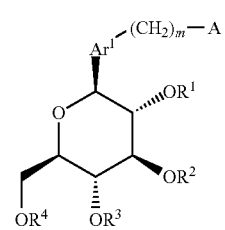

(Ib)

wherein A, $Ar^1$, $R^1$, $R^2$, $R^3$, $R^4$ and m are the same as above defined, or a prodrug or a pharmaceutically acceptable salt thereof.

According to a still further aspect of the present invention, there is provided a compound represented by formula (Ic):

[Formula 4]

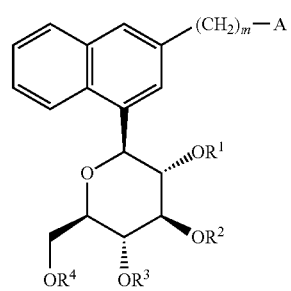

(Ic)

wherein A, $R^1$, $R^2$, $R^3$, $R^4$ and m are the same as above defined, or a prodrug or a pharmaceutically acceptable salt thereof.

Preferably, Rb in the present invention is independently selected from a $C_1$-$C_6$ alkyl group, a $C_1$-$C_6$ haloalkyl group, a halogen atom, a hydroxy group, a cyano group, a $C_1$-$C_6$ alkoxy group, a $C_1$-$C_6$ alkylthio group, a $C_1$-$C_6$ alkylsulfinyl group, a $C_1$-$C_6$ alkylsulfonyl group, and a $C_1$-$C_3$ alkylenedioxy group.

A is preferably a thienyl group or a benzothienyl group where these groups may be substituted with one or more Rb.

Furthermore, m in the present invention is preferably 1. In addition, $R^1$, $R^2$, $R^3$ and $R^4$ are each independently selected from a hydrogen atom and —C(=O)Rx, and Rx is a $C_1$-$C_6$ alkyl group which may be substituted with one or more Ra, or a $C_1$-$C_6$ alkoxy group which may be substituted with one or more Ra.

As the compound included in the present invention, for example, the following compound can be illustrated:

(2S,3R,4R,5S,6R)-2-[3-(benzo[b]thiophen-2-ylmethyl)-naphthalen-1-yl]-6-hydroxymethyl-tetrahydropyran-3,4,5-triol;

(2S,3R,4R,5S,6R)-2-[3-(5-fluorobenzo[b]thiophen-2-ylmethyl)naphthalen-1-yl]-6-hydroxymethyl-tetrahydropyran-3,4,5-triol;

(2S,3R,4R,5S,6R)-2-[3-(benzo[b]thiophen-2-ylmethyl)-4-methoxynaphthalen-1-yl]-6-hydroxymethyl-tetrahydropyran-3,4,5-triol;

(2R,3S,4R,5R,6S)-2-hydroxymethyl-6-[3-(5-methoxybenzo[b]-thiophen-2-ylmethyl)naphthalen-1-yl]tetrahydropyran-3,4,5-triol;

(2S,3R,4R,5S,6R)-2-[3-(5-ethylbenzo[b]thiophen-2-ylmethyl)naphthalen-1-yl]-6-hydroxymethyl-tetrahydropyran-3,4,5-triol;

(2S,3R,4R,5S,6R)-2-[3-(5-chlorobenzo[b]thiophen-2-ylmethyl)naphthalen-1-yl]-6-hydroxymethyl-tetrahydropyran-3,4,5-triol;

(2R,3S,4R,5R,6S)-2-hydroxymethyl-6-[3-(5-methylbenzo[b]-thiophen-2-ylmethyl)naphthalen-1-yl]tetrahydropyran-3,4,5-triol;

(2R,3S,4R,5R,6S)-2-hydroxymethyl-6-[3-(5-methylthiophen-2-ylmethyl)naphthalen-1-yl]tetrahydropyran-3,4,5-triol; and (2R,3S,4R,5R,6S)-2-hydroxymethyl-6-[3-(5-ethylthiophen-2-ylmethyl)naphthalen-1-yl]tetrahydropyran-3,4,5-triol.

According to another aspect of the present invention, there is provided a pharmaceutical composition comprising the above-described compound, a prodrug or a pharmaceutically acceptable salt thereof which is used as a $Na^+$-glucose cotransporter inhibitor.

According to a further aspect of the present invention, there is provided a pharmaceutical composition comprising the above-described compound, a prodrug or a pharmaceutically acceptable salt thereof which is used for the prophylaxis or therapy of diabetes [for example, insulin-dependent diabetes (type I diabetes) and insulin-independent diabetes (type II diabetes)], diabetic complications caused by hyperglycemia, or obesity.

According to a still further aspect of the present invention, there is provided a method of preventing or treating diabetes [for example, insulin-dependent diabetes (type I diabetes) and insulin-independent diabetes (type II diabetes)], diabetic complications caused by hyperglycemia, or obesity, which comprises administering an effective amount of the above-described compound, a prodrug or a pharmacologically acceptable salt thereof to a patient.

In the above-described formulae (I), (Ia), (Ib) and (Ic), the groups represented by $R^1$, $R^2$, $R^3$ and $R^4$ include, for example, a hydrogen atom, a $C_1$-$C_6$ alkyl group, a $C_1$-$C_6$ alkoxy $C_1$-$C_6$ alkyl group, a $C_7$-$C_{14}$ aralkyl group, a $C_1$-$C_6$ alkylcarbonyl group, a $C_7$-$C_{14}$ aralkylcarbonyl group, a $C_1$-$C_6$ alkoxycarbonyl group and a $C_7$-$C_{14}$ aralkyloxycarbonyl group. These groups may be substituted with one or more substituents, each independently selected from a halogen atom, a hydroxy group, a $C_1$-$C_6$ alkoxy group, a $C_1$-$C_6$ alkylcarbonyl group, a carboxyl group, an amino group, and a substituted amino group. As $R^1$, $R^2$, $R^3$ and $R^4$, a hydrogen atom or a $C_1$-$C_6$ alkylcarbonyl group is preferred, and a hydrogen atom is particularly preferred.

In the above-described formulae, $Ar^1$ may be substituted with, for example, one to four same or different substituents, for example, one to four substituents each independently selected from, a halogen atom; a hydroxy group; a $C_1$-$C_6$ alkyl group, a $C_3$-$C_8$ cycloalkyl group, a $C_1$-$C_6$ alkyoxy group, and a $C_1$-$C_6$ alkylthio group (these four groups may be substituted with one to four substituents selected from a halogen atom, a hydroxy group, and an amino group); a methylenedioxy group; a cyano group; a $C_1$-$C_6$ alkylsulfonyl group; a $C_1$-$C_6$ alkylsulfonylamino group; a nitro group; a carboxyl group; a substituted amino group; and a 4- to 6-membered heterocyclyl group.

In the above-described formulae, A may be substituted with one to four same or different substituents, for example, one to four substituents, each independently selected from a halogen atom; a hydroxy group; a $C_1$-$C_6$ alkyl group, a $C_3$-$C_8$ cycloalkyl group, a $C_1$-$C_6$ alkyloxy group and a $C_1$-$C_6$ alkylthio group (these four groups may be substituted with one to four substituents, each independently selected from a halogen atom, a hydroxy group and an amino group); a methylenedioxy group; a cyano group; a $C_1$-$C_6$ alkylsulfonyl group; a $C_1$-$C_6$ alkylsulfonylamino group; a nitro group; a carboxyl group; a substituted amino group; a 5- or 6-membered heteroaryl group; and a 4- to 6-membered heterocyclyl group.

The group represented by A includes, for example, a pyrrolyl group, an indolyl group, a pyridyl group, a quinolyl group, an isoquinolyl group, a thienyl group, a benzothienyl group, a furyl group, a benzofuranyl group, a thiazolyl group, a benzothiazolyl group, an isothiazolyl group, a benzoisothiazolyl group, a pyrazolyl group, an indazolyl group, an oxazolyl group, a benzoxazolyl group, an isoxazolyl group, a benzoisoxazolyl group, an imidazolyl group, a benzoimidazolyl group, a triazolyl group, a benzotriazolyl group, a pyrimidinyl group, a uracilyl group, a pyrazinyl group, a pyridazinyl group, an imidazopyridyl group, a triazolopyridyl group, and a pyrrolopyridyl group, and furthermore preferred are a thienyl group, a benzothienyl group, a furyl group, and benzofuranyl group, and moreover preferred are a thienyl group and a benzothienyl group. When A is a benzo-fused ring containing two or more rings, the group —$(CH_2)_m$— in the above-described formulae is connected on to a heterocycle in A.

The term "$C_1$-$C_6$ alkyl group" as used in this specification means a straight- or branched-chain alkyl group having 1 to 6 carbon atoms and includes, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl, and preferred $C_1$-$C_6$ alkyl groups include, for example, straight- or branched-chain alkyl groups having one to three carbon atoms, and particularly preferred are methyl and ethyl.

The term "$C_3$-$C_8$ cycloalkyl group" as used in this specification means a cyclic alkyl group having 3 to 8 carbon atoms and includes, for example, cyclopropyl, cyclobutyl, cyclopentyl, cyclohexyl, cycloheptyl and cyclooctyl.

The term "$C_1$-$C_6$ alkoxy group" as used in this specification means an alkyloxy group having a straight- or branched-chain alkyl group having one to six carbon atoms as the alkyl moiety and includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy and 3-ethylbutoxy.

The term "$C_7$-$C_{14}$ aralkyl group" as used in this specification means an arylalkyl group having 7 to 14 carbon atoms and containing an aryl group and includes, for example, benzyl, 1-phenethyl, 2-phenethyl, 1-naphthylmethyl and 2-naphthylmethyl.

The term "$C_7$-$C_{14}$ aralkyloxy group" as used in this specification means an arylalkyloxy group having 7 to 14 carbon atoms and containing the above defined aralkyl group and includes, for example, benzyloxy, 1-phenethyloxy, 2-phenethyloxy, 1-naphthylmethyloxy and 2-naphthyl-methyloxy.

The term "aryl group" as used in this specification means an aryl group having an aromatic hydrocarbon ring having six to ten carbon atoms and includes, for example, phenyl, 1-naphthyl and 2-naphthyl.

The term "heteroaryl group" as used in this specification means a 5- to 10-membered aromatic heterocyclic group containing one or more heteroatom independently selected from an oxygen atom, a nitrogen atom and a sulfur atom and includes, for example, furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidinyl, pyrazinyl, pyridazinyl, indolyl, quinolyl and isoquinolyl. Preferred heteroaryl groups are 5- to 6-membered heteroaryl groups such as a pyrrolyl group, a pyrazolyl group, an imidazolyl group and a pyridyl group, and particularly preferred is a pyrazolyl group.

The term "aryloxy group" as used in this specification means an aryloxy group having the above defined aromatic hydrocarbon group having six to ten carbon atoms as the aryl moiety and includes, for example, phenoxy, 1-naphthoxy and 2-naphthoxy.

The term "heteroaryloxy group" as used in this specification means a heteroaryloxy group having the above defined 5- to 10-membered aromatic heterocyclic group which contains one or more heteroatom selected from an oxygen atom, a nitrogen atom and a sulfur as the heteroaryl moiety and includes, for example, furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetra-zolyloxy, pyridinyloxy, pyrimidinyloxy, pyrazinyloxy, pyridazinyloxy, indolyloxy, quinolinyloxy and isoquino-linyloxy. Preferred heteroaryloxy groups are 5- to 6-membered heteroaryloxy groups.

The term "$C_1$-$C_6$ alkylamino group" as used in this specification means an alkylamino group having a straight- or branched-chain alkyl group having one to six carbon atoms as the alkyl moiety and includes, for example, methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentyl-amino, 1-methylpentylamino, 3-ethylbutylamino and 2-ethylbutylamino.

The term "di($C_1$-$C_6$ alkyl)amino group" as used in this specification means a dialkylamino group having straight- or branched-chain alkyl groups each having one to six carbon atoms as the two alkyl moieties which may be the same or different. The "di($C_1$-$C_6$ alkyl)amino group" includes, for example, dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino and ethyl-t-butylamino.

The term "$C_1$-$C_6$ alkylthio group" as used in this specification means an alkylthio group having a straight- or branched-chain alkyl group having one to six carbon atoms as the alkyl moiety and includes, for example, methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 2-ethylbutylthio and 2-ethylbutylthio.

The term "$C_1$-$C_6$ alkylsulfinyl group" as used in this specification means an alkylsulfinyl group (—SO—R) having a straight- or branched-chain alkyl group having one to six carbon atoms as the alkyl moiety and includes, for example, methylsulfinyl, ethylsulfinyl, n-propylsulfinyl, i-propylsulfinyl, n-butylsulfinyl, s-butylsulfinyl, i-butylsulfinyl, t-butylsulfinyl, n-pentylsulfinyl, 3-methylbutylsulfinyl, 2-methylbutylsulfinyl, 1-methyl-butylsulfinyl, 1-ethylpropylsulfinyl, n-hexylsulfinyl, 4-methylpentylsulfinyl, 3-methylpentylsulfinyl, 2-methyl-pentylsulfinyl, 1-methylpentylsulfinyl, 3-ethylbutyl-sulfinyl and 2-ethylbutylsulfinyl.

The term "$C_1$-$C_6$ alkylsulfonyl group" as used in this specification means an alkylsulfonyl group having a straight- or branched-chain alkyl group having one to six carbon atoms as the alkyl moiety and includes, for example, methylsulfonyl, ethylsulfonyl, n-propylsulfonyl, i-propyl-sulfonyl, n-butyl-sulfonyl, s-butylsulfonyl, i-butyl-sulfonyl, t-butylsulfonyl, n-pentylsulfonyl, 3-methyl-butylsulfonyl, 2-methylbutylsulfonyl, 1-methylbutyl-sulfonyl, 1-ethylpropylsulfonyl, n-hexylsulfonyl, 4-methylpentylsulfonyl, 3-methylpentyl-sulfonyl, 2-methyl-pentylsulfonyl, 1-methylpentylsulfonyl, 3-ethylbutyl-sulfonyl and 2-ethylbutylsulfonyl.

The group "—C(=O)—Rx" as used in this specification includes, for example, a $C_1$-$C_6$ alkylcarbonyl group, a $C_7$-$C_{14}$ aralkylcarbonyl group, a $C_1$-$C_6$ alkoxycarbonyl group and a $C_7$-$C_{14}$ aralkyloxycarbonyl group. Here, the $C_1$-$C_6$ alkylcarbonyl group includes, for example, an acetyl group, a propionyl group, butyryl group and pivaloyl, and particularly preferred is an acetyl group. The $C_7$-$C_{14}$ aralkylcarbonyl group includes, for example, benzyl-carbonyl group and naphthyl-methylcarbonyl group, and preferred is a benzylcarbonyl group.

The $C_1$-$C_6$ alkoxycarbonyl group includes, for example, a methoxycarbonyl group and an ethoxycarbonyl group, and preferred is a methoxycarbonyl group. The $C_7$-$C_{14}$ aralkyloxycarbonyl group includes, for example, a benzyloxycarbonyl group and a naphthylmethyloxycarbonyl group, and preferred is a benzyloxycarbonyl group.

The term "halogen atom" as used in this specification includes, for example, a fluorine atom, a chlorine atom, a bromine atom and an iodine atom.

The term "4- to 7-membered heterocycle" as used in this specification means a heterocycle which may be completely saturated or partially or completely unsaturated and contains one nitrogen and may further contain one or more heteroatom independently selected from an oxygen atom, a nitrogen atom and a sulfur atom and includes, for example, azetidine, pyrrolidine, piperidine and morpholine, and preferred is piperidine.

The term "aromatic carbon ring" as used in this specification means a 6- to 10-membered aromatic carbon ring and includes, for example, a benzene ring and a naphthalene ring.

The term "aromatic heterocycle" as used in this specification means a 5- to 6-membered aromatic heterocycle containing one or more heteroatom independently selected from an oxygen atom, a nitrogen atom and a sulfur atom and includes, for example, a pyrrole ring, an indole ring, a thiophene ring, a benzothiophene ring, a furan ring, a benzofuran ring, a pyridine ring, a quinoline ring, an isoquinoline ring, a thiazole ring, a benzothiazole ring, an isothiazole ring, a benzoisothiazole ring, a pyrazole ring, an indazole ring, an oxazole ring, a benzoxazole ring, an isoxazole ring, a benzoisoxazole ring, an imidazole ring, a benzoimidazole ring, a triazole ring, a benzotriazole ring, a pyrimidine ring, a uracil ring, a pyrazine ring and a pyridazine ring.

The term "substituted amino group" as used in this specification includes, for example, —NReRf (wherein Re is a hydrogen atom, a $C_1$-$C_6$ alkyl group, a $C_1$-$C_6$ alkylcarbonyl group, a carbamoyl group or a $C_1$-$C_6$ alkoxycarbonyl group; Rf is a hydrogen atom or a $C_1$-$C_6$ alkyl group; and Re and Rf may form a 4- to 7-membered heterocycle together with the nitrogen atom to which they are bonded).

The term "$C_1$-$C_3$ alkylenedioxy group" as used in this specification is a divalent group represented by the formula: —O—($C_1$-$C_3$ alkylene)-O— and includes, for example, a methylenedioxy group, an ethylenedioxy group and a dimethylenedioxy group.

The term "heterocyclyl group" as used in this specification means a 4- to 7-membered heterocyclyl group which contains one or more heteroatom independently selected from an oxygen atom, a nitrogen atom and a sulfur atom and may be completely saturated or partially or completely unsaturated and includes, for example, azetidinyl, pyrrolidinyl, piperidinyl, piperazinyl, pyrrolyl, imidazolyl, imidazolinyl, pyrazolyl, pyrazolinyl, oxazolinyl, morphorinyl, thiomorphorinyl, pyridyl, pyrazinyl, pyrimidinyl, pyridazinyl, hexamethyleneimino, furyl, tetrahydrofuryl, thienyl, tetrahydrothienyl, dioxolanyl, oxothiolanyl, and dioxanyl. The substitution position on the heterocyclyl group is not particularly limited as far as it is the substitutable position on a carbon atom or a nitrogen atom.

Further, the compounds of the present invention include tautomers, mixtures of various types of stereoisomers such as optical isomers and their isolated isomers.

The compounds of the present invention sometimes form acid addition salts. Further depending on the type of the substituent, they sometimes form salts with bases. Such salts include, for example, acid addition salts of mineral acids such as hydrochloric acid, hydrobromic acid, hydroiodic acid, sulfuric acid, nitric acid and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid; acidic amino acids such as asparaginic acid and glutamic acid. Further, salts formed with bases include salts with inorganic bases such as sodium, potassium, magnesium, calcium and aluminum; salts with organic bases such as methylamine, ethylamine and ethanolamine; salts with basic amino acids such as lysine and ornithine; and ammonium salts.

Furthermore, the compounds of the present invention include the hydrates and pharmaceutically acceptable various solvates, polymorphs and the like.

Further, the compounds of the present invention are not limited to the compounds as will be described in the Examples below and include all glucitol derivatives represented by the above-described formula (I) and their pharmaceutically acceptable salts.

Further, the present invention includes the compounds which are converted to the compounds represented by the above-described formula (I) by the metabolism in a living body and their pharmaceutically acceptable salts, that is, so-called prodrugs. The groups which form the prodrugs of the compounds of the present invention include, for example, those described in Prog. Med., 5, 2157-2161 (1985) and those described in *Development of Drugs,* 7 (Molecular Designing), 163-198, Hirokawa Shoten, 1990.

The compounds of the present invention can be produced by applying various known synthetic methods depending on the characteristic features based on the type of the basic skeleton or the substituent. In this instance, when there is a case such that the group is preferably protected with an appropriate protective group at the stage of the starting material or an intermediate from a production technique viewpoint, the protective group can be eliminated in later steps to obtain a desired compound. The groups which require protection in the production step include, for example, a hydroxy group and a carboxyl group, and the protective groups for these groups include the protective groups described in Greene and Wuts, *Protective Groups in Organic Synthesis,* 2nd edition. The protective group used and the reaction conditions for introducing and eliminating the protective group are suitably selected based on known techniques such as the above-described documents.

The compounds of the present invention have an inhibitory activity of sodium-dependent glucose transporter 2 (SGLT2) (J. Clin. Invest., 93, 397 (1994)) relating to the renal glucose reabsorption. By the inhibition of the glucose reabsorption, excess glucose is excreted and hyperglycemia is remedied without giving a load on the β-cells of the pancreas to bring about a therapeutic effect on diabetes and an improved effect on insulin resistance.

Thus, according to one aspect of the present invention, there is provided a medicament for preventing or treating a disease or a condition which can be improved by inhibiting the SGLT2 activity, for example, diabetes, diabetes-related diseases and diabetic complications.

The term "diabetes" as used herein includes, type I diabetes, type II diabetes and other types of diabetes due to specific causes. Further, the term "diabetes-related diseases" as used herein include, for example, obesity, hyperinsulinism, saccharometabolic disorder, hyperlipidemia, hypercholesterolemia, hypertriglyceridemia, lipogranulomatosis, hypertension, congestive heart failure, edema, hyperuricemia and gout.

Further, the term "diabetic complications" as used herein include both acute complications and chronic complications. The "acute complications" include, for example, hyperglycemia (ketoacidosis and the like) and infectious diseases (such as skin, soft tissues, biliary tract, respiratory system and urinary tract) and the "chronic complications" include, for example, microangio-pathy (nephropathy and retinopathy), arteriosclerosis (such as atherosclerosis, myocardial infarction, cerebral thrombosis and lower limbo arterial obstruction), neuro-pathy (such as a sensory nerve, a motor nerve and an autonomic nerve) and foot gangrene. The major diabetic complications include, for example, diabetic retinopathy, diabetic nephropathy and diabetic neuropathy.

Further, the compounds of the present invention can be used in combination with a diabetes treating agent, a diabetic complication therapeutic agent, a hyperlipidemia therapeutic agent, a hypertension therapeutic agent or the like which has a mechanism of action different than that of SGLT2 activity inhibitors. By combining the compounds of the present invention with the other agents, an additive effect can be expected compared to the effect obtained from each single agent in the above diseases.

The "diabetes therapeutic agents and diabetic complication therapeutic agents" which are usable in combination include, for example, insulin sensitivity enhancers (such as PPAR γ agonist, PPAR α/γ agonist, PPAR δ agonist and PPAR α/γ/δ agonist), glycosidase inhibitors, biguanide drugs, insulin secretion promoters, insulin preparations, glucagon receptor antagonists, insulin receptor kinase promoters, tripeptiydyl peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose bisphosphatase inhibitors, pyruvate dehydrogenase inhibitors, glucokinase activators, D-chiro-inositol, glycogen synthase kinase 3 inhibitors, glucagon-like peptide 1, glucagon-like peptide-1 analogs, glucagon-like peptide-1 agonists, amyrin, amyrin analogs, amyrin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKK β inhibitors, lipido-peroxidase inhibitors, N-acetylated-α-linked-acid-dipeptidase inhibitors, insulin-like growth factor-I, platelet-derived growth factor (PDGF), platelet-derived growth factor (PDGF) analogs, epidermal growth factor (EGF), nerve growth factor, carnitine derivatives, uridine, 5-hydroxy-1-methylhydantoin, EGB-761, bimoclomol, sulodexide, Y-128 and TAR-428.

As the diabetes therapeutic agents and the diabetic complication therapeutic agents, the following are illustrated.

"Biguanide drugs" include, for example, metformin hydrochloride and phenformin.

Among "insulin secretion promoters", sulfonylureas include, for example, glyburide (glibenclamide), glipizide, glyclazide and chlorpropamide, and non-sulfonylureas include, for example, nateglinide, repaglinide and mitiglinide.

"Insulin preparations" include recombinant human insulin and animal-derived insulin, and are classified into three groups according to the time of action, that is, the immediate-acting type (human insulin and human neutral insulin), the medium type (an insulin-human isophane insulin aqueous suspension, a human neutral insulin-human isophane insulin aqueous suspension, a human insulin zinc aqueous suspension and an insulin zinc aqueous suspension) and the enlonged-acting type (a human crystalline insulin zinc suspension).

"Glycosidase inhibitors" include, for example, acarbose, voglibose and miglitol.

PPAR γ agonists of "insulin sensitivity enhancers" include, for example, troglitazone, pioglytazone and rosiglytazone, and PPAR α/γ dual agonists include, for example, MK-767 (KRP-297), tesaglitazar, LM 4156, LY 510929, DRF-4823 and TY-51501, and PPAR δ agonists include, for example, GW-501516.

"Tripeptidyl peptidase II inhibitors" include, for example, UCL-139.

"Dipeptidyl peptidase IV inhibitors" include, for example, NVP-DPP728A, LAF-237, MK-0431, P32/98 and TSL-225.

"Aldose reductase inhibitors" include, for example, ascorbyl gamolenate, tolrestat, epalrestat, fidarestat, sorbinil, ponalrestat, risarestat and zenarestat.

"γ-Aminobutyric acid receptor antagonists" include, for example, topiramate.

"Sodium channel antagonists" include, for example, mexiletin hydrochloride.

"Transcription factor NF-κB inhibitors" include, for example, dexlipotam.

"Lipoperoxidase inhibitors" include, for example, tirilazad mesylate.

"N-Acetylated α-linked-acid-dipeptidase inhibitors" include, for example, GPI-5693.

"Carnitine derivatives" include, for example, carnitine and levacecarnine hydrochloride.

"Hyperlipidemia therapeutic agents and the hypertension therapeutic agents" which can be used in combination include, for example, hydroxymethylglutaryl coenzyme A reductase inhibitors, fibrate compounds, $\beta_3$-adrenaline receptor agonists, AMPK activators, acyl coenzyme A: cholesterol acyl transferase inhibitors, probucol, thyroid hormone receptor agonists, cholesterol absorption inhibitors, lipase inhibitors, microsome triglyceride transfer protein inhibitors, lipoxygenase inhibitors, carnitine palmitoyl transferase inhibitors, squalene synthase inhibitors, low density lipoprotein receptor promoters, nicotinic acid derivatives, bile acid adsorbents, sodium conjugated bile acid transporter inhibitors, cholesteryl ester transfer protein inhibitors, angiotensin converting enzyme inhibitors, angiotensin II receptor antagonists, endothelin converting enzyme inhibitors, endothelin receptor antagonists, diuretics, calcium antagonists, vasodilating hypotensive agents, sympathetic blocking agents, central hypotensive agents, $\alpha_2$-adrenergic receptor agonists, antiplatelet agents, uric acid formation inhibitors, uric acid excretion stimulants, urine alkalifying agents, anorectics, adiponectin receptor agonists, GPR40 agonists and GPR40 antagonists.

As the hyperlipidemia therapeutic agents and the hypertension therapeutic agents, the following are illustrated.

"Hydroxymethylglutaryl coenzyme A reductase inhibitors" include, for example, fluvastatin, lovastatin, pravastatin, cerivastatin and pitavastatin.

"Fibrate compounds" include, for example, bezafibrate, beclobrate and binifibrate.

"Squalene synthase inhibitors" include, for example, TAK-475, α-phosphonosulfonate derivatives (as described in U.S. Pat. No. 5,712,396).

"Acyl coenzyme A: cholesterol acyl transferase inhibitors" include, for example, CI-1011, NTE-122, FCE-27677, RP-73163, MCC-147 and DPU-129.

"Low density lipoprotein receptor promoters" include, for example, MD-700 and LY-295427.

"Microsome triglyceride transfer protein inhibitors (MTP inhibitors)" include, for example, compounds as described in the specifications of U.S. Pat. Nos. 5,739,135, 5,712,279, 5,760,246 and the like.

"Anorectics" include, for example, adrenaline-noradrenaline agonists (mazindol, ephedrine and the like), serotonin agonists (selective serotonin retake inhibitors such as fluvoxamine), adrenalin.serotnin agonists (sibutramine and the like), melanocortin 4 receptor (MC4R) agonists and α-melanocyte concentrating hormones (α-MCH), leptin, cocaine- and amphetamine-regulated transcript (CART) and the like.

"Thyroid hormone receptor agonists" include, for example, lyothyronine sodium and levothyroxine sodium.

"Cholesterol adsorption inhibitors" include, for example, ezetimibe.

"Lipase inhibitors" include, for example, orlistat.

"Carnitine palmitoyl transferase inhibitors" include, for example, etomoxir.

"Nicotinic acid derivatives" include, for example, nicotinic acid, nicotinamide, nicomol and nicorandil.

"Bile acid adsorbents" include, for example, cholestyramine, cholestilan and cholesevelam hydrochloride.

"Angiotensin-converting enzyme inhibitors" include, for example, captopril, enalapril maleate, aracepril and cilazapril.

"Angiotensin II receptor antagonists" include, for example, candesartan cilexetil, losartan potassium and eprosartan mesylate.

"Endothelin-converting enzyme inhibitors" include, for example, CGS-31447 and CGS-35066.

"Endothelin receptor antagonists" include, for example, L-749805, TBC-3214 and BMS-182874.

For example, in the therapy of diabetes and the like, it is suitable that the compounds of the present invention are used together with at least one agent selected from the group consisting of insulin sensitivity enhancers (PPAR γ agonists, PPAR α/γ agonists, PPAR δ agonists, PPAR α/γ/δ agonists and the like), glycosidase inhibitors, biguanide drugs, insulin secretion promoters, insulin preparations and dipeptidyl peptidase IV inhibitors.

Further, it is suitable that the compounds of the present invention are used together with at least one agent selected from the group consisting of hydroxymethyl-glutaryl coenzyme A reductase inhibitors, fibrate compounds, squalene synthetase inhibitors, acyl coenzyme A: cholesterol acyl transferase inhibitors, low density lipoprotein receptor promoters, microsome triglyceride transfer protein inhibitors and anorectics.

The drugs of the present invention can be administered systemically or topically or orally or parenterally (for example, rectally, subcutaneously, intramuscularly, intravenously or percutaneously).

The compounds of the present invention which are used as drugs may be in any form of a solid composition, a liquid composition and another composition, and the most suitable form is selected as necessary. The drugs of the present invention can be produced by incorporating a pharmaceutically acceptable carrier into the compounds of the present invention. Specifically, an excipient, a filler, a binder, a disintegrator, a coating agent, a sugar-coating agent, a pH adjustor, a solubilizing agent which is conventionally used or an aqueous or nonaqueous solvent is added to the compounds of the present invention to prepare tablets, pills, capsules, granule, dusting powders, powders, liquids and solutions, emulsions, suspensions, injections or the like by the conventionally employed techniques for pharmaceutical formulations. The excipients and fillers include, for example, lactose, magnesium stearate, starch, talc, gelatin, agar, pectin, acacia, olive oil, sesame oil, cacao butter, ethylene glycol and other substances usually used.

Further, the compounds of the present invention can be made into formulations by forming clathrate compounds with α-, β- or γ-cyclodextrin or methylated cyclodextrin.

The dose of the compounds of the present invention varies depending on the disease, the status of the disease, weight, age, sex and the route of administration, and is preferably 0.1 to 1,000 mg/kg weight/day, more preferably 0.1 to 200 mg/kg weight/day and can be administered once a day or dividedly several times a day.

The compounds of the present invention can be synthesized, for example, by the production methods as shown below.

The compounds of the present inventions can be synthesized by the method as shown in Scheme 1.

Scheme 1

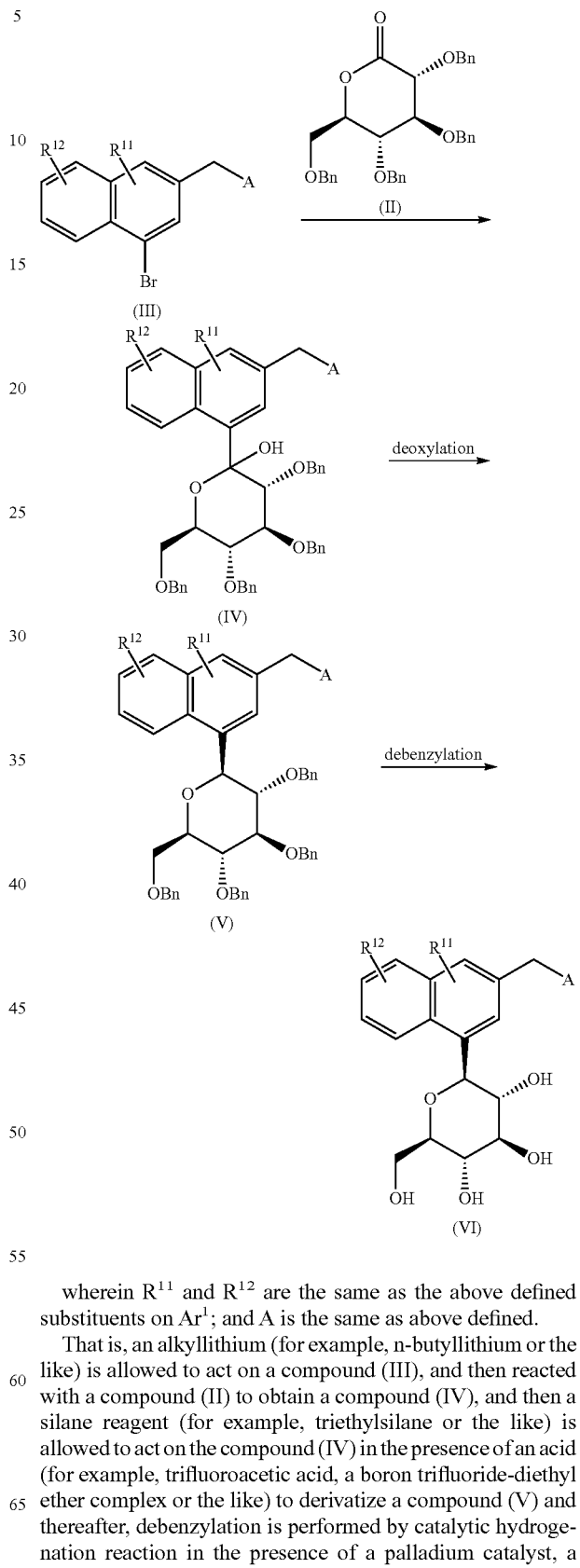

wherein $R^{11}$ and $R^{12}$ are the same as the above defined substituents on $Ar^1$; and A is the same as above defined.

That is, an alkyllithium (for example, n-butyllithium or the like) is allowed to act on a compound (III), and then reacted with a compound (II) to obtain a compound (IV), and then a silane reagent (for example, triethylsilane or the like) is allowed to act on the compound (IV) in the presence of an acid (for example, trifluoroacetic acid, a boron trifluoride-diethyl ether complex or the like) to derivatize a compound (V) and thereafter, debenzylation is performed by catalytic hydrogenation reaction in the presence of a palladium catalyst, a method of using a Lewis acid (boron tribromide, boron trichloride, a boron trichloride-dimethylsulfide complex, a boron trifluoride-diethyl ether complex and ethanethiol, a boron trifluoride-diethyl ether complex and dimethylsulfide or the like) or the like to produce a compound (VI). Further, the compound (II) can be synthesized, for example, by the method as described in a document [Carbohydr. Res., 260, 243 (1994)], and the compound (III) can be synthesized, for example, by the method as described in patent documents (International Publication Nos. WO01/27128 and WO04/013118).

The compounds of the present invention can be also produced by the method of Scheme 2.

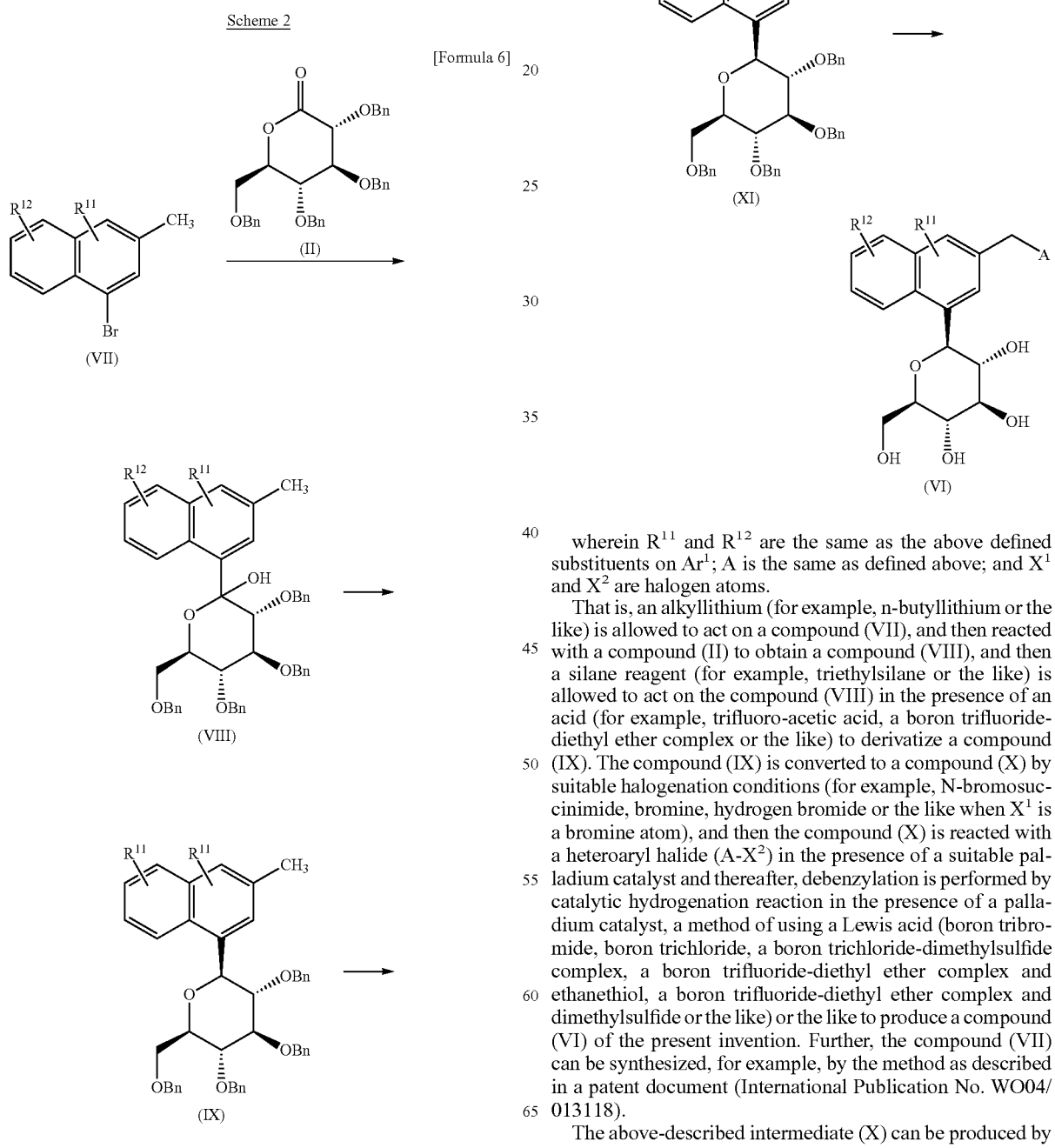

wherein $R^{11}$ and $R^{12}$ are the same as the above defined substituents on $Ar^1$; A is the same as defined above; and $X^1$ and $X^2$ are halogen atoms.

That is, an alkyllithium (for example, n-butyllithium or the like) is allowed to act on a compound (VII), and then reacted with a compound (II) to obtain a compound (VIII), and then a silane reagent (for example, triethylsilane or the like) is allowed to act on the compound (VIII) in the presence of an acid (for example, trifluoro-acetic acid, a boron trifluoride-diethyl ether complex or the like) to derivatize a compound (IX). The compound (IX) is converted to a compound (X) by suitable halogenation conditions (for example, N-bromosuccinimide, bromine, hydrogen bromide or the like when $X^1$ is a bromine atom), and then the compound (X) is reacted with a heteroaryl halide (A-$X^2$) in the presence of a suitable palladium catalyst and thereafter, debenzylation is performed by catalytic hydrogenation reaction in the presence of a palladium catalyst, a method of using a Lewis acid (boron tribromide, boron trichloride, a boron trichloride-dimethylsulfide complex, a boron trifluoride-diethyl ether complex and ethanethiol, a boron trifluoride-diethyl ether complex and dimethylsulfide or the like) or the like to produce a compound (VI) of the present invention. Further, the compound (VII) can be synthesized, for example, by the method as described in a patent document (International Publication No. WO04/013118).

The above-described intermediate (X) can be produced by the following method.

Scheme 3

[Formula 7]

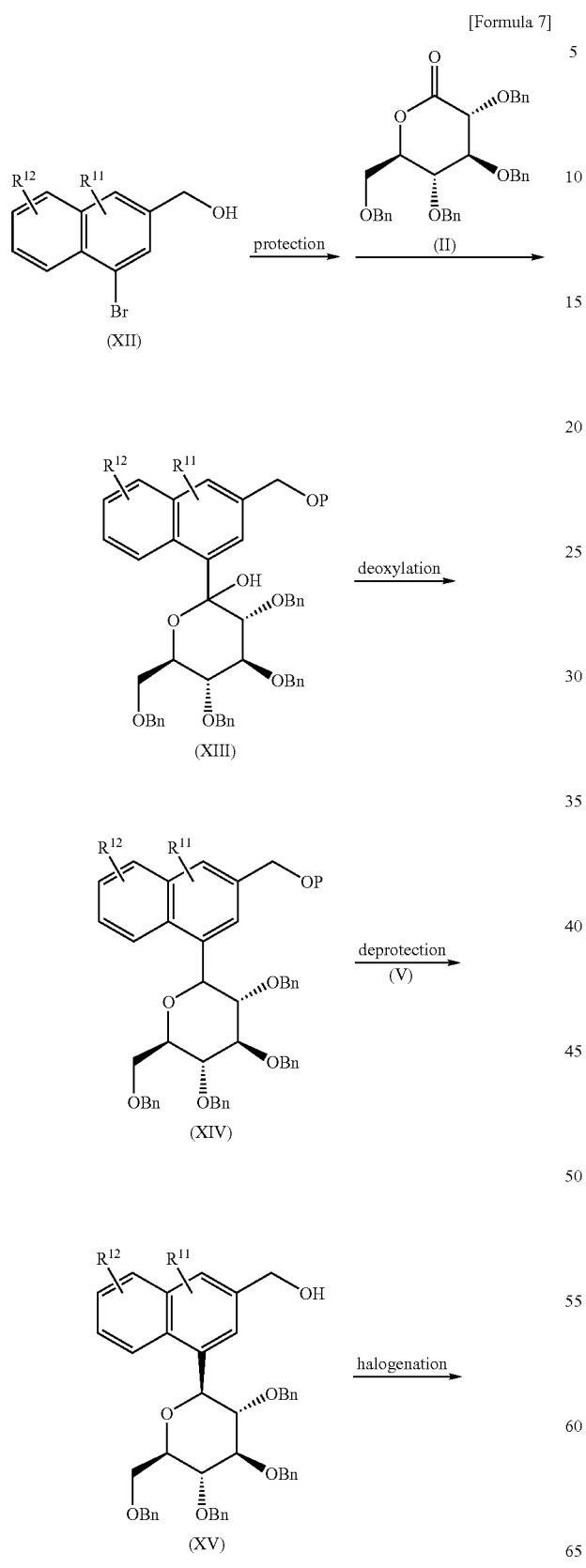

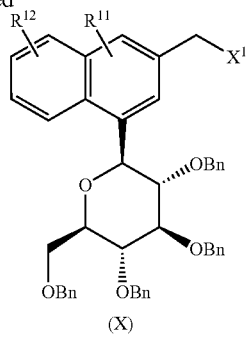

wherein $R^{11}$ and $R^{12}$ are the same as the above defined substituents on $Ar^1$; A is the same as defined above; P is a protective group for the hydroxy group; and $X^1$ is a halogen atom.

That is, the hydroxy group of a compound (XII) is protected with a suitable protective group P (for example, a tert-butyldimethylsilyl group, a tetrahydropyranyl group or the like), and then a suitable alkyllithium (for example, n-butyllithium or the like) is allowed to act on the resulting compound, and then reacted with a compound (II) to derivatize a compound (XIII). Then, a silane reagent (for example, triethylsilane or the like) is allowed to act on the compound (XIII) in the presence of an acid (for example, trifluoroacetic acid, a boron trifluoride-diethyl ether complex or the like) to derivatize a compound (XIV). Then, deprotection is performed to obtain a compound (XV), and thereafter the obtained compound is subjected to suitable halogenation conditions (conditions of using N-bromosuccinimide, bromine, carbon tetrabromide or the like in the presence of triphenylphosphine) to synthesize a compound (X).

The compounds of the present invention can be also produced by the method of Scheme 4.

Scheme 4

[Formula 8]

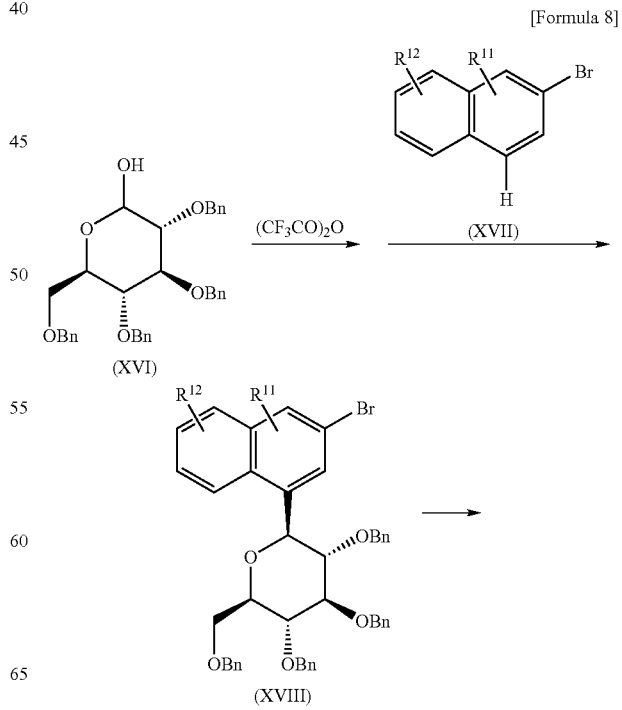

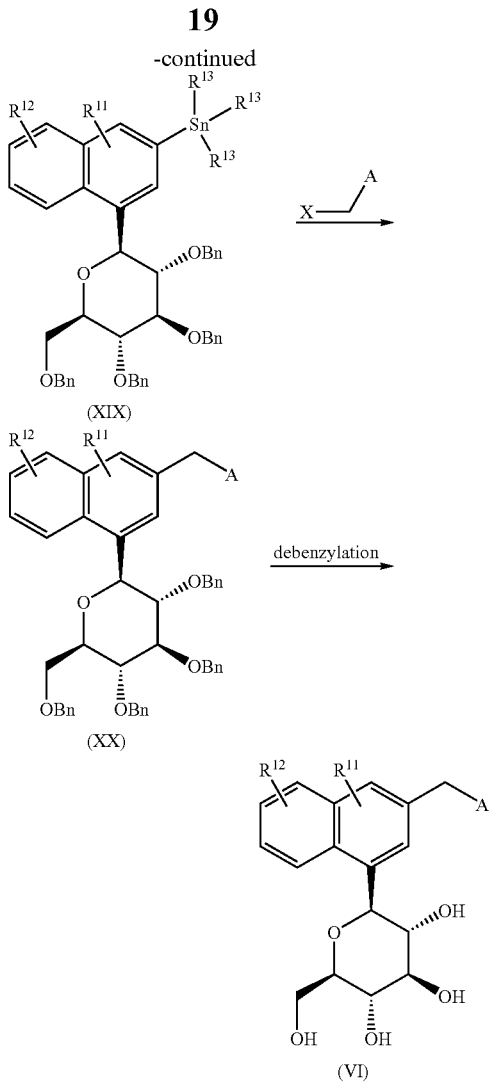

wherein $R^{11}$ and $R^{12}$ are the same as the above defined substituents on $Ar^1$; $R^{13}$ is each independently selected from a $C_1$-$C_6$ alkyl group (for example, a butyl group or the like); A is the same as defined above; and X is a halogen atom.

If necessary, in the presence of a suitable base (for example, sodium acetate or the like), an acid anhydride (for example, trifluoroacetic anhydride or the like) is allowed to act on a compound (XVI), and then reacted with a compound (XVII) in the presence of a suitable Lewis acid (for example, a boron trifluoride-diethyl ether complex or the like) to obtain a compound (XVIII). Then, the compound (XVIII) is reacted with a hexaalkylditin (for example, hexabutylditin or the like) in the presence of a suitable palladium catalyst to derivatize a compound (XIX) which is thereafter reacted with A-CH$_2$—X (wherein A is the same as defined above; and X is a halogen atom) in the presence of a suitable palladium catalyst to obtain a compound (XX). Thereafter, debenzylation is performed by catalytic hydrogenation reaction in the presence of a palladium catalyst, a method of using a Lewis acid (boron tribromide, boron trichloride, a boron trichloride-dimethylsulfide complex, a boron trifluoride-diethyl ether complex and ethanethiol, a boron trifluoride-diethyl ether complex and dimethylsulfide or the like) or the like to produce a compound (VI).

The method for producing the compounds of the present invention is not limited to the above-described methods. The compounds of the present invention can be also produced, for example, by suitably combining the steps included in the Schemes 1 to 4.

EXAMPLES

The contents of the present invention will be explained in further details by the following examples and experimental examples but the present invention is not limited to their contents.

Each abbreviation in the following examples has the following meaning.

NMR: Nuclear magnetic resonance spectrum (TMS internal standard);
MS: Mass spectrometric analysis value;
HPLC: High-performance liquid chromatography;
NMR, MS and HPLC were measured by the following equipment.
NMR: JOEL JNM-EX-270 (270 MHz) or Brucker ARX 300 (300 MHz);
MS: LCQ of Thermo Finigan or Micromass ZQ or Quattro micro of Waters;
HPLC: 2690/2996 (Detector) of Waters.

Example 1

(2S,3R,4R,5S,6R)-2-[3-(Benzo[b]thiophen-2-ylmethyl)-naphthalen-1-yl]-6-hydroxymethyl-tetrahydropyran-3,4,5-triol (1) Synthesis of (Benzo[b]thiophen-2-yl)-(4-bromonaphthalen-2-yl)methanol Under a nitrogen atmosphere, an n-butyllithium hexane solution (1.6 M, 2.04 ml, 3.27 mmol) was added dropwise to a solution of benzothiophene (0.48 g, 3.58 mmol) in anhydrous THF (10 ml) at −78° C. over 5 minutes. The reaction solution was stirred at −78° C. for 10 minutes, and then at room temperature for 20 minutes. A solution of 4-bromonaphathalene-2-carbaldehyde (0.73 ml, 3.11 mmol) in anhydrous THF (5 ml) was added dropwise to the resulting reaction mixture at −78° C. and stirred at −78° C. for two hours. To the reaction mixture, a saturated ammonium chloride aqueous solution was added and the resulting mixture was extracted with diethyl ether, and the organic layer was washed with a saturated sodium chloride aqueous solution and then dried with anhydrous magnesium sulfate. After filtration, the solvent was distilled under reduced pressure and the obtained residue was purified by silica gel flash column chromatography [n-hexane:ethyl acetate (10:1)] to obtain the title compound (1.0 g, 75.6%).

$^1$H-NMR (CDCl$_3$) δ: 2.72 (1H, d, J=3.9 Hz), 6.22 (1H, d, J=3.6 Hz), 7.17 (1H, s), 7.25-7.36 (2H, m), 7.52-7.70 (3H, m), 7.77 (1H, d, J=7.5 Hz), 7.83 (1H, d, J=7.8 Hz), 7.84 (1H, s), 7.92 (1H, s), 8.21 (1H, d, J=8.1 Hz)

(2) Synthesis of 2-(4-Bromonaphthalen-2-ylmethyl)benzo-[b]thiophene

In a nitrogen stream, triethylsilane (0.48 ml, 3.01 mmol) and a boron trifluoride-diethyl ether complex (0.34 ml, 2.71 mmol) were added dropwise to a solution of (benzo[b]-thiophen-2-yl)-(4-bromonaphthalen-2-yl)methanol (1.0 g, 2.71 mmol) in methylene chloride (30 mL) at 0° C. The reaction mixture was stirred at room temperature for three hours, and then a 50% methanol aqueous solution (1 ml) was added and further water was added thereto and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:40)] to obtain the title compound (0.82 g, 85.6%).

$^1$H-NMR (CDCl$_3$) δ: 4.34 (2H, s), 7.05 (1H, s), 7.23-7.33 (2H, m), 7.48-7.59 (2H, m), 7.66-7.79 (5H, m), 8.19 (1H, d, J=8.1 Hz)

(3) Synthesis of (3R,4S,5S,6R)-2-[3-(Benzo[b]thiophen-2-ylmethyl)naphthalen-1-yl]-3,4,5-trisbenzyloxy-6-benzyloxymethyltetrahydropyran-2-ol Under a nitrogen atmosphere, an n-butyllithium hexane solution (1.6 M, 1.58 ml, 2.53 mmol) was added dropwise to a solution of 2-(4-bromonaphthalen-2-ylmethyl)-benzo[b]thiophene (0.81 g, 2.29 mmol) in anhydrous THF (15 ml) at −78° C. over five minutes. The reaction mixture was stirred at −78° C. for 5 minutes, and then a solution of 3,4,5-trisbenzyloxy-6-benzyloxymethyltetrahydropyran-2-one (1.36 g, 2.52 mmol) in anhydrous THF (10 ml) was added dropwise thereto at −78° C. and the reaction solution was stirred at −78° C. for 2 hours. To the obtained reaction mixture was added a saturated ammonium chloride aqueous solution and the mixture was extracted with diethyl ether and the organic layer was washed with a saturated sodium chloride aqueous solution, and then dried with anhydrous magnesium sulfate. After filtration, the solvent was distilled under reduced pressure and the obtained residue was purified by silica gel flash column chromatography [n-hexane:ethyl acetate (10:1)] to obtain the title compound (1.4 g, 75%).

$^1$H-NMR (CDCl$_3$) δ: 3.47 (1H, d, J=10.5 Hz), 3.52 (1H, s), 3.74 (1H, d, J=10.2 Hz), 3.98 (1H, d, J=9.0 Hz), 4.10-4.28 (4H, m), 4.35 (2H, s), 4.46 (1H, d, J=11.7 Hz), 4.59 (1H, d, J=12 Hz), 4.76 (1H, d, J=10.8 Hz), 4.88 (2H, s), 4.97 (1H, d, J=10.8 Hz), 6.66 (2H, d, J=7.2 Hz), 6.94 (2H, t, J=7.5 Hz), 7.05 (2H, d, J=7.5 Hz), 7.21-7.33 (18H, m), 7.42 (1H, t, J=7.5 Hz), 7.62 (1H, d, J=7.2 Hz), 7.68 (1H, d, J=7.8 Hz), 7.75 (1H, s), 7.80 (1H, d, J=7.8 Hz), 7.89 (1H, d, J=1.8 Hz), 8.63 (1H, d, J=8.7 Hz)

MS (ESI$^+$): 836 [M+Na]$^+$ (4) Synthesis of (2S,3R,4R,5S,6R)-2-[3-(Benzo[b]thiophen-2-ylmethyl)naphthalen-1-yl]-3,4,5-trisbenzyloxy-6-benzyloxymethyltetrahydropyran In a nitrogen stream, triethylsilane (0.34 ml, 2.06 mmol) and a boron trifluoride-diethyl ether complex (0.24 ml, 1.89 mmol) were added dropwise to a solution of (3R,4S,5S,6R)-2-[3-(benzo[b]thiophen-2-ylmethyl)naphthalen-1-yl]-3,4,5-trisbenzyloxy-6-benzyloxymethyltetrahydropyran-2-ol (1.4 g, 1.72 mmol) in methylene chloride (15 ml) at 0° C. The reaction mixture was stirred at room temperature for two hours, and then water was added thereto and extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate n-hexane (1:10)] to obtain the title compound (1.1 g, 80.2%).

$^1$H-NMR (CDCl$_3$) δ: 3.42 (1H, d, J=10.2 Hz), 3.66-3.96 (6H, m), 4.09 (1H, d, J=10.2 Hz), 4.37 (2H, s), 4.51 (1H, d, J=12.3 Hz), 4.63 (1H, d, J=12 Hz), 4.69 (1H, d, J=10.8 Hz), 4.87-4.96 (4H, m), 6.50 (2H, d, J=7.2 Hz), 6.96 (2H, t, J=7.8, 7.2 Hz), 7.03 (1H, s), 7.06 (1H, d, J=7.5 Hz), 7.21-7.30 (17H, m), 7.37-7.50 (2H, m), 7.60 (2H, s), 7.68 (1H, d, J=7.8 Hz), 7.74 (1H, s), 7.82 (1H, d, J=7.5 Hz), 8.38 (1H, d, J=8.4 Hz)

MS (ESI$^+$): 820 [M+Na]$^+$ (5) Synthesis of (2S,3R,4R,5S,6R)-2-[3-(Benzo[b]thiophen-2-ylmethyl)naphthalen-1-yl]-6-hydroxymethyltetrahydro-pyran-3,4,5-triol In a nitrogen stream, dimethylsulfide (3.5 ml) and boron trifluoride-diethyl ether complex (1.75 ml, 13.8 mmol) were added dropwise to an solution of (2S,3R,4R,5S,6R)-2-[3-(benzo[b]thiophen-2-ylmethyl)naphthalen-1-yl]-3,4,5-trisbenzyloxy-6-benzyloxymethyltetrahydropyran (1.1 g, 1.38 mmol) in anhydrous methylene chloride (30 ml) at 0° C. and the reaction mixture was stirred at room temperature for three days. Water (10 ml) was added thereto and the resulting mixture was then extracted with methylene chloride. The organic layer was washed with a saturated sodium chloride aqueous solution and dried with anhydrous magnesium sulfate. After filtration, the solvent was distilled under reduced pressure, and the obtained residue was purified by silica gel flash column chromatography [methylene chloride:methanol (30:1)] to obtain the title compound (0.35 g, 58.2%).

$^1$H-NMR (CD$_3$OD) δ: 3.63-3.51 (3H, m), 3.69-3.81 (2H, m), 3.90 (1H, d, J=12 Hz), 4.40 (2H, s), 4.90 (1H, d, J=9.3 Hz), 7.11 (1H, s), 7.20-7.30 (2H, m), 7.44-7.49 (2H, m), 7.64-7.74 (4H, m), 7.81 (1H, d, J=8.4 Hz), 8.27 (1H, d, J=8.1 Hz)

MS (ESI$^+$): 459 [M+Na]$^+$

Example 2

(2S,3R,4R,5S,6R)-2-[3-(5-Fluorobenzo[b]thiophen-2-yl-methyl)naphthalen-1-yl]-6-hydroxymethyl-tetrahydropyran-3,4,5-triol (1) Synthesis of 1-(2,2-Dimethoxyethylsulfanyl)-4-fluorobenzene In a nitrogen stream, 4-fluorobenzenethiol (2.5 ml, 23.4 mmol) and 2-bromo-1,1-dimethoxyethane (3.0 ml, 25.7 mmol) were added to a sodium methoxide methanol solution (0.5 M, 74.9 ml, 37.4 mmol) under cooling with ice and the reaction mixture was stirred at the same temperature for 10 minutes, and then heated and refluxed for five hours. The reaction mixture was concentrated under reduced pressure, and added with cold water. The mixture was extracted with ether. The organic layer was washed with a saturated sodium chloride aqueous solution, and then dried with sodium sulfate. After filtration, the solvent was distilled under reduced pressure, and the obtained residue was purified by silica gel column chromatography [developing solution=ethyl acetate: n-hexane (1:20)] to obtain the title compound (4.52 g, 89%).

$^1$H-NMR (CDCl$_3$) δ: 3.05 (2H, d, J=5.4 Hz), 3.35 (6H, s), 4.49 (1H, t, J=5.4 Hz), 6.85 (2H, t, J=9.0 Hz), 7.31 (2H, dd, J=8.7, 5.1 Hz)

(2) Synthesis of 5-Fluorobenzo[b]thiophene

Under a nitrogen atmosphere, polyphosphoric acid (10 g) was added to anhydrous chlorobenzene (150 ml). Under refluxing, 1-(2,2-diemthoxyethylsulfanyl)-4-fluorobenzene (4.0 g, 18.5 mmol) was added to the resulting solution over 1.5 hours, and the obtained solution was heated to reflux overnight. The reaction mixture was cooled to room temperature, and then an organic layer was separated. To the polyphosphoric acid layer was added water and extracted with methylene chloride. All organic layers thus obtained were washed with water and a saturated sodium chloride aqueous solution and dried with sodium sulfate. After filtration, the solvent was distilled under reduced pressure, and the obtained residue was purified by silica gel column chromatography [developing solution=ethyl acetate:n-hexane (1:50)] to obtain the title compound (420 mg, 15%).

$^1$H-NMR (CDCl$_3$) δ: 7.10 (1H, dt, J=8.7, 2.4 Hz), 7.27 (1H, dd, J=12.6, 7.2 Hz), 7.45-7.54 (2H, m), 7.77 (1H, dd, J=8.7, 4.8 Hz).

(3) Synthesis of 4-Bromonaphthalene-2-carbaldehyde

Under a nitrogen atmosphere, an oxalyl chloride methylene chloride solution (2.0 M, 4.88 ml) was diluted with methylene chloride (40 ml), and dimethyl sulfoxide (0.9 ml, 12.7 mmol) was added dropwise thereto at −78° C. To this solution, a solution of (4-bromonaphthalene-2-yl)-methanol (1.15 g, 4.88 mmol) as synthesized according to a document [J. Med. Chem., 37, 2485 (1993)] in methylene chloride (10 ml) was added dropwise over 10 minutes. This reaction mixture was stirred at −78° C. for 15 minutes and −45° C. for one hour, and then triethylamine (4.0 ml, 29.3 mmol) was added dropwise thereto and stirred at 0° C. for 30 minutes. To the reaction solution, a saturated ammonium chloride aqueous solution was added and the resulting solution was extracted with methylene chloride. The organic layer was washed with water and a saturated sodium chloride aqueous solution, and dried with sodium sulfate. After filtration, the solvent was distilled under reduced pressure, and the obtained residue was purified by silica gel column chromatography [developing solution=ethyl acetate:n-hexane (1:20)] to obtain the title compound (890 mg, 78%).

$^1$H-NMR (CDCl$_3$) δ: 7.66 (1H, t, J=7.7 Hz), 7.78 (1H, t, J=8.0 Hz), 8.21 (1H, d, J=8.0 Hz), 8.27-8.33 (3H, m), 10.11 (1H, s)

(4) Synthesis of (4-Bromonaphthalen-2-yl)-(5-fluorobenzo-[b]thiophen-2-yl)methanol In a nitrogen stream, an n-butyllithium hexane solution (1.6 M, 1.68 ml, 2.68 mmol) was added dropwise to a solution of 5-fluorobenzo[b]thiophene (410 mg, 2.68 mmol) in THF (10 ml) and the reaction solution was stirred at the same temperature for 10 minutes. To this solution, a solution of 4-bromonaphthalene-2-carbaldehyde (600 mg, 2.55 mmol) in THF (5 ml) was added dropwise at −78° C. The obtained mixture was stirred at the same temperature for two hours, and then a saturated ammonium chloride aqueous solution was added and the mixture was extracted with ether. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (680 mg, 69%).

$^1$H-NMR (CDCl$_3$) δ: 2.75 (1H, d, J=3.9 Hz), 6.20 (1H, d, J=3.6 Hz), 7.04 (1H, dt, J=9.0, 2.4 Hz), 7.11 (1H, s), 7.33 (1H, dd, J=9.3, 2.7 Hz), 7.48-7.63 (2H, m), 7.68 (1H, dd, J=8.7, 4.8 Hz), 7.82-7.94 (3H, m), 8.21 (1H, d, J=8.4 Hz)

(5) Synthesis of 2-(4-Bromonaphthalen-2-ylmethyl)-5-fluorobenzo[b]thiophene

In a nitrogen stream, triethylsilane (0.18 ml, 2.11 mmol) and a boron trifluoride-diethyl ether complex (0.25 ml, 1.94 mmol) were added to a solution of (4-bromo-naphthalen-2-yl)-(5-fluorobenzo[b]-thiophen-2-yl)methanol (260 mg, 0.65 mmol) in methylene chloride (10 ml) at 0° C. and the mixture was stirred a room temperature for two hours. A saturated sodium hydrogen carbonate aqueous solution was added and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:100)] to obtain the title compound (520 mg, 80%).

$^1$H-NMR (CDCl$_3$) δ: 4.32 (2H, s), 7.02 (2H, dt, J=9.0, 2.4 Hz), 7.25-7.82 (7H, m), 8.20 (1H, d, J=9.0 Hz)

(6) Synthesis of (3R,4S,5S,6R)-3,4,5-Trisbenzyloxy-6-benzyloxymethyl-2-[3-(5-fluorobenzo[b]thiophen-2-ylmethyl)naphthalen-1-yl]tetrahydropyran-2-ol In a nitrogen stream, an n-butyllithium hexane solution (1.6 M, 0.97 ml, 1.55 mmol) was added dropwise to a solution of 2-(4-bromonaphthalen-2-yl-methyl)-5-fluorobenzo[b]thiophene (520 mg, 1.41 mmol) in THF (15 ml) at −78° C. and the reaction mixture was stirred at the same temperature for 10 minutes. To this solution, a solution of 3,4,5-trisbenzyloxy-6-benzyloxymethyl-tetrahydropyran-2-one (835 mg, 1.55 mmol) in THF (3 ml) was added dropwise. The mixture was stirred at −78° C. for one hour, and a saturated ammonium chloride aqueous solution was added thereto to stop the reaction. The reaction mixture was extracted with ether, and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:20)] to obtain the title compound (770 mg, 66%).

$^1$H-NMR (CDCl$_3$) δ: 3.48 (1H, d, J=10.8 Hz), 3.52 (1H, s), 3.75 (1H, d, J=10.2 Hz), 4.00 (1H, d, J=10.5 Hz), 4.05 (1H, d, J=10.5 Hz), 4.10-4.28 (4H, m), 4.34 (2H, s), 4.47 (1H, d, J=12.0 Hz), 4.59 (1H, d, J=12.0 Hz), 4.76 (1H, d, J=10.8 Hz), 4.88 (2H, s), 4.97 (1H, d, J=10.8 Hz), 6.67 (1H, d, J=6.9 Hz), 6.94-7.07 (4H, m), 7.22-7.37 (19H, m), 7.43 (1H, t, J=7.5 Hz), 7.57 (1H, dd, J=8.7, 4.8 Hz), 7.75 (1H, s), 7.80 (1H, d, J=8.1 Hz), 7.87 (1H, s), 8.64 (1H, d, J=8.7 Hz)

(7) Synthesis of (3R,4R,5S,6R)-3,4,5-Trisbenzyloxy-6-benzyloxymethyl-2-[3-(5-fluorobenzo[b]thiophen-2-ylmethyl)naphthalen-1-yl]tetrahydropyran In a nitrogen stream, triethylsilane (0.19 ml, 1.21 mmol) and a boron trifluoride-diethyl ether complex (0.14 ml, 1.11 mmol) were added to a solution of (3R,4R,5S,6R)-3,4,5-trisbenzyloxy-6-benzyloxymethyl-2-[3-(5-fluorobenzo-[b] thiophen-2-ylmethyl)-naphthalen-1-yl]tetrahydropyran-2-ol (770 mg, 0.93 mmol) in methylene chloride (10 ml) at 0° C. The reaction mixture was stirred at room temperature for two hours, and then a saturated sodium hydrogen carbonate aqueous solution was added. The obtained mixture was extracted with methylene chloride, and the organic layer was washed with a saturated sodium chloride aqueous solution and then dried with sodium sulfate. The solvent was distilled under reduced pressure, and the obtained residue was purified by silica gel column chromatography [developing solution=ethyl acetate:n-hexane (1:20)] to obtain the title compound (550 mg, 73%).

$^1$H-NMR (CDCl$_3$) δ: 3.43 (1H, d, J=10.2 Hz), 3.79-3.93 (6H, m), 4.10 (1H, d, J=10.5 Hz), 4.35 (2H, s), 4.51 (1H, d,

J=12.0 Hz), 4.62 (1H, d, J=12.3 Hz), 4.69 (1H, d, J=10.8 Hz), 4.89-4.92 (4H, m), 6.50 (2H, d, J=7.2 Hz), 6.94-7.07 (5H, m), 7.21-7.59 (20H, m), 7.74 (1H, s), 7.83 (1H, d, J=8.1 Hz), 8.38 (1H, d, J=8.4 Hz)

(8) Synthesis of (2S,3R,4R,5S,6R)-2-[3-(5-Fluorobenzo[b]-thiophen-2-ylmethyl)naphthalen-1-yl]-6-hydroxymethyl-tetrahydropyran-3,4,5-triol Under a nitrogen atmosphere, dimethylsulfide (1.72 ml) and a boron trifluoride-diethyl ether complex (0.86 ml, 6.8 mmol) were added to a solution of (3R,4R,5S,6R)-3,4,5-trisbenzyloxy-6-benzyloxymethyl-2-[3-(5-fluorobenzo[b]-thiophen-2-ylmethyl)naphthalen-1-yl]tetrahydropyran (550 mg, 0.68 mmol) in methylene chloride (15 ml) under cooling with ice. The reaction mixture was stirred at room temperature for 2.5 days, then a saturated sodium hydrogen carbonate aqueous solution was added under cooling with ice and the mixture was extracted with methylene chloride. The organic layer was washed with a saturated sodium chloride aqueous solution and then dried with sodium sulfate, and thereafter the solvent was distilled under reduced pressure. The obtained residue was purified by silica gel column chromatography [developing solution=methylene chloride:methanol (40:1)] to obtain the title compound (140 mg, 46%).

$^1$H-NMR (CD$_3$OD) δ: 3.51-3.80 (5H, m), 3.90 (1H, d, J=6.0 Hz), 4.39 (2H, s), 4.90 (1H, d, J=9.6 Hz), 7.01 (1H, dt, J=8.7, 2.1 Hz), 7.09 (1H, s), 7.37 (1H, dt, J=8.7, 2.1 Hz), 7.44-7.49 (2H, s), 7.63-7.73 (3H, m), 7.80 (1H, d, J=6.0 Hz), 8.28 (1H, d, J=8.7 Hz)

MS (ESI$^+$): 477 [M+Na]$^+$

Example 3

(2S,3R,4R,5S,6R)-2-[3-(Benzo[b]thiophen-2-ylmethyl)-4-methoxynaphthalen-1-yl]-6-hydroxymethyl-tetrahydropyran-3,4,5-triol (1) Synthesis of 2,4-Dibromo-1-methoxynaphthalene Under a nitrogen atmosphere, bromine (9.88 ml, 192.8 mmol) was added to a solution of 1-methoxynaphthalene (15.3 g, 96.4 mmol) in methylene chloride (450 ml) at room temperature over 10 minutes. The reaction mixture was stirred at room temperature for two hours, then a saturated Na$_2$S$_2$O$_5$ aqueous solution was added and the mixture was extracted with methylene chloride. The organic layer was washed with a saturated sodium chloride aqueous solution and dried (anhydrous magnesium sulfate), and then the solvent was distilled under reduced pressure to obtain the title compound (29.4 g, 98%).

$^1$H-NMR (CDCl$_3$) δ: 4.00 (3H, s), 7.59-7.65 (2H, m), 7.91 (1H, s), 8.12-8.20 (2H, m)

(2) Synthesis of 4-Bromo-1-methoxynaphthalene-2-carbaldehyde

In a nitrogen stream, an n-butyllithium hexane solution (1.6 M, 56.9 ml, 91.1 mmol) was added dropwise to a solution of 2,4-dibromo-1-methoxy-naphthalene (30.3 g, 95.9 mmol) in THF (1,800 ml) at −78° C. and the reaction mixture was stirred at the same temperature for 30 minutes. To this mixture, N,N-dimethylformamide (8.9 ml, 115.1 mmol) was added at −78° C. The mixture was stirred at the same temperature for three hours, and then a saturated ammonium chloride aqueous solution was added thereto and the mixture was extracted with ether. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:8)] to obtain the title compound (3.85 g, 15%).

$^1$H-NMR (CDCl$_3$) δ: 4.15 (3H, s), 7.64-7.79 (2H, m), 8.16 (1H, s), 8.26-8.29 (2H, m), 10.52 (1H, s)

(3) Synthesis of Benzo[b]thiophen-2-yl-(4-bromo-1-methoxy-naphthalen-2-yl)methanol In a nitrogen stream, an n-butyllithium hexane solution (1.6 M, 6.2 ml, 9.90 mmol) was added dropwise to a solution of benzothiophene (1.33 g, 9.90 mmol) in THF (20 ml) at −78° C. and the reaction mixture was stirred at the same temperature for 10 minutes. To this mixture, a solution of 4-bromo-1-methoxynaphthalene-2-carbaldehyde (2.5 g, 9.43 mmol) in THF (30 ml) was added dropwise at −78° C. The reaction mixture was stirred at the same temperature for two hours, and then a saturated ammonium chloride aqueous solution was added thereto and the mixture was extracted with ether. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:4)] to obtain the title compound (3.12 g, 83%).

$^1$H-NMR (CDCl$_3$) δ: 3.08 (1H, d, J=4.8 Hz), 3.91 (3H, s), 6.58 (1H, d, J=4.1 Hz), 7.14 (1H, s), 7.28-7.35 (2H, m), 7.57-7.69 (3H, m), 7.77-7.81 (1H, m), 7.95 (1H, s), 8.10-8.25 (2H, m)

(4) Synthesis of 2-(4-Bromo-1-methoxynaphthalen-2-yl-methyl)benzo[b]thiophene

In a nitrogen stream, triethylsilane (2.48 ml, 15.5 mmol) and a boron trifluoride-diethyl ether complex (1.08 ml, 8.54 mmol) were added dropwise to a solution of benzo[b]thiophen-2-yl-(4-bromo-1-methoxynaphthalen-2-yl)methanol (3.1 g, 7.76 mmol) in methylene chloride (60 ml) at 0° C. and the reaction mixture was stirred at room temperature for two hours, and then a 50% methanol aqueous solution (1 ml) was added and furthermore water (30 ml) was added thereto. The resulting mixture was extracted with methylene chloride, and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate: n-hexane (1:50)] to obtain the title compound (2.38 g, 80%).

$^1$H-NMR (CDCl$_3$) δ: 3.95 (3H, s), 4.41 (2H, s), 7.04 (1H, s), 7.22-7.33 (2H, m), 7.56-7.75 (5H, m), 8.13-8.21 (2H, m)

(5) Synthesis of (3R,4R,5S,6R)-2-[3-(Benzo[b]thiophen-2-ylmethyl)-4-methoxynaphthalen-1-yl]-3,4,5-tris-benzyloxy-6-benzyloxymethyltetrahydropyran-2-ol In a nitrogen stream, an n-butyllithium hexane solution (1.6 M, 1.09 ml, 1.75 mmol) was added dropwise to a solution of 2-(4-bromo-1-methoxynaphthalen-2-ylmethyl)-benzo[b]thiophene (610 mg, 1.59 mmol) in THF (9 ml) at −78° C. The reaction mixture was stirred at the same temperature for five minutes, and to this solution, a solution of 3,4,5-trisbenzyloxy-6-benzyloxmethyltetrahydro-pyran-2-one (940 mg, 1.75 mmol) in THF (3 ml) was added dropwise and the resulting mixture was stirred at −78° C. for two hours. A saturated ammonium chloride aqueous solution was added thereto to stop the reaction. The obtained reaction mixture was extracted with ether, and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate n-hexane (1:6)] to obtain the title compound (859 mg, 64%).

$^1$H-NMR (CDCl$_3$) δ: 3.45-4.98 (20H, m), 6.66-7.67 (27H, m), 7.87 (1H, s), 8.16 (1H, d, J=7.5 Hz), 8.63 (1H, d, J=8.7 Hz)

(6) Synthesis of (3R,4R,5S,6R)-2-[3-(Benzo[b]thiophen-2-ylmethyl)-4-methoxynaphthalen-1-yl]-3,4,5-tris-benzyloxy-6-benzyloxymethyltetrahydropyran In a nitrogen stream, triethylsilane (0.33 ml, 2.04 mmol) and a boron trifluoride-diethyl ether complex (0.14 ml, 1.12 mmol) were added dropwise to a solution of (3R,4R,5S,6R)-2-[3-(benzo[b]thiophen-2-ylmethyl)-4-methoxynaphthalen-1-yl]-3,4,5-trisbenzyloxy-6-benzyloxy-methyltetrahydropyran-2-ol (859 mg, 1.02 mmol) in methylene chloride (17 ml) at 0° C. The reaction mixture was stirred at room temperature for one hour, and then water (20 ml) added thereto. The obtained mixture was extracted with methylene chloride, and the organic layer was washed with a saturated sodium chloride aqueous solution and dried with sodium sulfate. The solvent was distilled under reduced pressure and the obtained residue was purified by silica gel column chromatography [developing solution=ethyl acetate:n-hexane (1:10)] to obtain the title compound (517 mg, 61%).

$^1$H-NMR (CDCl$_3$) δ: 3.52-4.89 (20H, m), 6.51 (2H, d, J=7.5 Hz), 6.93-7.67 (26H, m), 8.18 (1H, d, J=8.7 Hz), 8.39 (1H, d, J=8.7 Hz)

(7) Synthesis of (2S,3R,4R,5S,6R)-2-[3-(Benzo[b]thiophen-2-ylmethyl)-4-methoxynaphthalen-1-yl]-6-hydroxymethyl-tetrahydropyran-3,4,5-triol Under a nitrogen atmosphere, dimethylsulfide (1.6 ml) and a boron trifluoride-diethyl ether complex (0.79 ml, 6.23 mmol) were added to a solution of (3R,4R,5S,6R)-2-[3-(benzo[b]thiophen-2-ylmethyl)-4-methoxynaphthalen-1-yl]-3,4,5-trisbenzyloxy-6-benzyloxymethyltetrahydropyran (515 mg, 0.62 mmol) in methylene chloride (10 ml) under cooling with ice. The reaction mixture was stirred at room temperature for three days, then water (10 ml) was added under cooling with ice and the mixture was extracted with methylene chloride. The organic layer was washed with a saturated sodium chloride aqueous solution and then dried with sodium sulfate, and thereafter the solvent was distilled under reduced pressure. The obtained residue was purified by silica gel column chromatography [developing solution=methylene chloride:methanol (20:1)] to obtain the title compound (82 mg, 28%).

$^1$H-NMR (CD$_3$OD) δ: 3.49-3.90 (7H, m), 3.94 (3H, m), 4.48 (2H, d, J=6.0 Hz), 7.11 (1H, s), 7.22-7.76 (7H, m), 8.16-8.19 (1H, m), 8.33-8.36 (1H, m)

MS (ESI$^-$): 465 [M−1]$^-$

Example 4

(2R,3S,4R,5R,6S)-2-Hydroxymethyl-6-[3-(5-methoxybenzo-[b]thiophen-2-ylmethyl)naphthalen-1-yl]tetrahydropyran-3,4,5-triol (1) Synthesis of 1-(2,2-Dimethoxyethylsulfanyl)-4-methoxy-benzene Under a nitrogen atmosphere, 4-methoxybenzenethiol (3.07 ml, 25.0 mmol) and 2-bromo-1,1-dimethoxyethane (3.25 ml, 27.5 mmol) were added to a sodium methoxide methanol solution (0.5 M, 80.0 ml, 40.0 mmol) under cooling with ice. The reaction mixture was stirred at the same temperature for 10 minutes, and then heated to reflux for five hours. The reaction mixture was concentrated under reduced pressure and cold water was added. The resulting mixture was extracted with ether, and the organic layer was washed with a saturated sodium chloride aqueous solution and then dried with sodium sulfate. After filtration, the solvent was distilled under reduced pressure, and the obtained residue was purified by silica gel column chromatography [developing solution=ethyl acetate:n-hexane (1:20)] to obtain the title compound (5.30 g, 93%).

$^1$H-NMR (CDCl$_3$) δ: 3.00 (2H, d, J=5.6 Hz), 3.33 (6H, s), 3.70 (3H, s), 4.47 (1H, t, J=5.6 Hz), 6.85 (2H, d, J=8.8 Hz), 7.39 (2H, d, J=8.8 Hz)

(2) Synthesis of 5-Methoxybenzo[b]thiophene

Under a nitrogen atmosphere, polyphosphoric acid (10 g) was added to anhydrous chlorobenzene (150 ml). To the resulting mixture, 1-(2,2-dimethoxyethylsulfanyl)-4-methoxybenzene (5.2 g, 22.7 mmol) was added under refluxing over 1.5 hours and the reaction mixture was heated to reflux overnight. The reaction was cooled to room temperature, and then the organic layer was separated. To the polyphosphoric acid layer, water was added and the obtained solution was extracted with methylene chloride. All organic layers thus obtained were washed with water and a saturated sodium chloride aqueous solution and dried with sodium sulfate. After filtration, the solvent was distilled under reduced pressure, and the obtained residue was purified by silica gel column chromatography [developing solution=ethyl acetate:n-hexane (1:40)] to obtain the title compound (1.1 g, 30%).

$^1$H-NMR (CDCl$_3$) δ: 3.51 (3H, s), 7.00 (1H, dd, J=8.8, 2.4 Hz), 7.26 (2H, m), 7.44 (1H, d, J=5.5 Hz), 7.73 (1H, d, J=8.8 Hz)

(3) Synthesis of (4-Bromonaphthalen-2-yl)-(5-methoxybenzo-[b]thiophen-2-yl)methanol In a nitrogen stream, an n-butyllithium hexane solution (1.6 M, 1.48 ml, 2.36 mmol) was added dropwise to a solution of 5-methoxybenzo[b]thiophene (388 mg, 2.36 mmol) in THF (6 ml) at −78° C. and the reaction solution was stirred at the same temperature for 10 minutes. To this solution, a solution of 4-bromonaphthalene-2-carbaldehyde (530 mg, 2.25 mmol) in THF (4 ml) was added dropwise. The reaction mixture was stirred at the same temperature for two hours, and then a saturated ammonium chloride aqueous solution added and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (725 mg, 77%).

$^1$H-NMR (CDCl$_3$) δ: 2.62 (1H, d, J=4.0 Hz), 3.83 (3H, s), 6.22 (1H, d, J=3.8 Hz), 6.95 (1H, dd, J=8.8, 2.5 Hz), 7.10 (1H, s), 7.15 (1H, d, J=2.5 Hz), 7.52-7.65 (3H, m), 7.83-7.88 (2H, m), 7.93 (1H, s), 8.22 (1H, d, J=8.1 Hz)

(4) Synthesis of 2-(4-Bromonaphthalen-2-ylmethyl)-5-fluorobenzo[b]thiophene

In a nitrogen stream, (4-bromonaphthalen-2-yl)-(5-methoxybenzo[b]thiophen-2-yl)methanol (260 mg, 0.65 mmol) was added dropwise to an solution of trimethylsilyl iodide (0.46 ml, 3.26 mmol) in acetonitrile (10 ml) at 0° C. over two hours, and the reaction mixture was stirred at the same temperature for one hour. A saturated sodium hydrogen carbonate aqueous solution was added and the resulting mixture was extracted with ethyl acetate. The organic layer was washed with a sodium thiosulfate aqueous solution and a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:10)] to obtain the title compound (130 mg, 52%).

$^1$H-NMR (CDCl$_3$) δ: 3.84 (3H, s), 4.32 (2H, s), 6.91 (2H, dd, J=8.8, 2.5 Hz), 6.98 (1H, s), 7.14 (1H, d, J=2.5 Hz), 7.51-7.61 (3H, m), 7.70-7.79 (3H, m), 8.19 (1H, d, J=8.2 Hz)

(5) Synthesis of (2R,3S,4R,5R)-3,4,5-Trisbenzyloxy-2-benzyloxymethyl-6-[3-(5-methoxybenzo[b]thiophen-2-ylmethyl)naphthalen-1-yl]tetraydropyran-6-ol In a nitrogen stream, an n-butyllithium hexane solution (1.6 M, 0.31 ml, 0.50 mmol) was added dropwise to a solution of 2-(4-bromonaphthalen-2-yl-methyl)-5-methoxybenzo[b]thiophene (173 mg, 0.45 mmol) in THF (15 ml) at −78° C. and the reaction mixture was stirred at the same temperature for 10 minutes and to this solution, a solution of 3,4,5-trisbenzyloxy-6-benzyloxymethyl-tetrahydropyran-2-one (267 mg, 0.50 mmol) in THF (2 ml). The reaction solution was stirred at −78° C. for one hour, and a saturated ammonium chloride aqueous solution was added to stop the reaction. The obtained reaction solution was extracted with ethyl acetate and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate n-hexane (1:4)] to obtain the title compound (279 mg, 73%).

$^1$H-NMR (CDCl$_3$) δ: 3.46-3.50 (2H, m), 3.74 (1H, d, J=10.6 Hz), 3.82 (3H, s), 4.00 (1H, d, J=10.4 Hz), 4.05 (1H, d, J=10.4 Hz), 4.10-4.28 (4H, m), 4.34 (2H, s), 4.47 (1H, d, J=11.9 Hz), 4.59 (1H, d, J=11.9 Hz), 4.76 (1H, d, J=10.8 Hz), 4.88 (2H, s), 4.96 (1H, d, J=10.8 Hz), 6.67 (1H, d, J=7.3 Hz), 6.88-6.98 (4H, m), 7.04-7.09 (2H, m), 7.21-7.35 (16H, m), 7.42 (1H, t, J=7.2 Hz), 7.53 (1H, d, J=8.8 Hz), 7.75 (1H, s), 7.79 (1H, d, J=8.0 Hz), 7.88 (1H, d, J=1.6 Hz), 8.65 (1H, d, J=8.7 Hz)

(6) Synthesis of (2R,3S,4R,5R)-3,4,5-Trisbenzyloxy-2-benzyloxymethyl-6-[3-(5-methoxybenzo[b]thiophen-2-ylmethyl)naphthalen-1-yl]tetrahydropyran In a nitrogen stream, trimethylsilane (0.093 ml, 0.58 mmol) and a boron trifluoride-diethyl ether complex (0.041 ml, 0.32 mmol) were added to a solution of (2R,3S,4R,5R)-3,4,5-trisbenzyloxy-2-benzyloxymethyl-6-[3-(5-methoxybenzo-[b]thiophen-2-ylmethyl)naphthalen-1-yl]tetrahydropyran-6-ol (245 mg, 0.29 mmol) in methylene chloride (3 ml) at 0° C. The reaction mixture was stirred at room temperature for one hour, and then a saturated sodium hydrogen carbonate aqueous solution was added. The resulting mixture was extracted with methylene chloride, and the organic layer was washed with a saturated sodium chloride aqueous solution and dried with sodium sulfate. The solvent was distilled under reduced pressure, and the obtained residue was purified by silica gel column chromatography [developing solution=ethyl acetate:n-hexane (1:6)] to obtain the title compound (271 mg, 80%).

$^1$H-NMR (CDCl$_3$) δ: 3.42 (1H, d, J=10.2 Hz), 3.63-3.99 (9H, m), 4.09 (1H, d, J=9.9 Hz), 4.35 (2H, s), 4.52 (1H, d, J=12.2 Hz), 4.63 (1H, d, J=12.2 Hz), 4.69 (1H, d, J=10.8 Hz), 4.87-4.96 (4H, m), 6.50 (2H, d, J=7.3 Hz), 6.88 (1H, dd, J=7.2, 2.4 Hz), 6.95-6.99 (3H, m), 7.05-7.10 (2H, m), 7.21-7.30 (15H, m), 7.37-7.50 (2H, m), 7.53 (1H, d, J=8.8 Hz), 7.60 (1H, s), 7.74 (1H, s), 7.82 (1H, d, J=7.7 Hz), 8.37 (1H, d, J=8.2 Hz)

(7) Synthesis of (2R,3S,4R,5R,6S)-2-Hydroxymethyl-6-[3-(5-methoxybenzo[b]thiophen-2-ylmethyl)naphthalen-1-yl]-tetrahydropyran-3,4,5-triol Under a nitrogen atmosphere, dimethylsulfide (0.66 ml) and a boron trifluoride-diethyl ether complex (0.33 ml, 2.62 mmol) were added to a solution of (2R,3S,4R,5R)-3,4,5-trisbenzyloxy-2-benzyloxymethyl-6-[3-(5-methoxybenzo-[b]thiophen-2-ylmethyl)-naphthalen-1-yl]tetrahydropyran (217 ml, 0.262 mmol) in methylene chloride (4 ml) under cooling with ice. The reaction mixture was stirred at room temperature for three days, and then a saturated sodium hydrogen carbonate aqueous solution was added under cooling with ice and the mixture was extracted with methylene chloride. The organic layer was washed with a saturated sodium chloride aqueous solution and dried with sodium sulfate, and then the solvent was distilled under reduced pressure and the obtained residue was purified by silica gel column chromatography [developing solution=methylene chloride:methanol (30:1)] to obtain the title compound (85 mg, 65%).

$^1$H-NMR (CD$_3$OD) δ: 3.51-3.63 (3H, m), 3.69-3.80 (5H, m), 3.90 (1H, d, J=11.6 Hz), 4.37 (2H, s), 4.90 (1H, d, J=9.5 Hz), 6.87 (1H, dd, J=8.8, 2.5 Hz), 7.04 (1H, s), 7.19 (1H, d, J=2.4 Hz), 7.43-7.49 (2H, m), 7.57 (1H, d, J=8.8 Hz), 7.63 (1H, s), 7.73 (1H, s), 7.79-7.82 (1H, m), 8.27 (1H, d, J=9.3 Hz)

MS (ESI$^+$): 489 [M+Na]$^+$

Example 5

(2S,3R,4R,5S,6R)-2-[3-(5-Ethylbenzo[b]thiophen-2-yl-methyl)naphthalen-1-yl]-6-hydroxymethyl-tetrahydropyran-3,4,5-triol (1) Synthesis of 1-(2,2-Dimethoxyethylsulfanyl)-4-ethyl-benzene Under a nitrogen atmosphere, 4-ethylbenzenethiol (3.50 ml, 25.4 mmol) and 2-bromo-1,1-dimethoxyethane (3.3 ml, 27.9 mmol) were added to a sodium methoxide methanol solution (0.5 M, 81.4 ml, 40.7 mmol) under cooling with ice. The reaction mixture was stirred at the same temperature for 10 minutes, and then heated to reflux for five hours. The reaction mixture was concentrated under reduced pressure, and cold water was added. The resulting mixture was extracted with ether and the organic layer was washed with a saturated sodium chloride aqueous solution and dried with sodium sulfate. After filtration, the solvent was distilled under reduced pressure and the obtained residue was purified by silica gel column chromatography [developing solution=ethyl acetate:n-hexane (1:20)] to obtain the title compound (5.31 g, 93%).

$^1$H-NMR (CDCl$_3$) δ: 1.22 (3H, t, J=7.6 Hz), 2.62 (2H, q, J=7.6 Hz), 3.08 (2H, d, J=5.6 Hz), 3.36 (6H, s), 4.51 (1H, t, J=5.6 Hz), 7.12 (2H, d, J=8.3 Hz), 7.32 (2H, d, J=8.3 Hz)

(2) Synthesis of 5-Ethylbenzo[b]thiophene

Under a nitrogen atmosphere, polyphosphoric acid (10 g) was added to anhydrous chlorobenzene (150 ml). To the resulting solution, 1-(2,2-dimthoxyethylsulfanyl)-4-ethylbenzene (5.31 g, 23.5 mmol) was added under refluxing over 1.5 hours and continued heating to reflux overnight. The reaction mixture was cooled to room temperature, and then the organic layer was separated. Water was added to the polyphosphoric acid layer and the resulting mixture was extracted with methylene chloride. All organic layers thus obtained were washed with water and a saturated sodium chloride aqueous solution and dried with sodium sulfate. After filtration, the solvent was distilled under reduced pressure, and the obtained residue was purified by silica gel column chromatography [developing solution=ethyl acetate:n-hexane (1:20)] to obtain the title compound (0.98 g, 26%).

$^1$H-NMR (CDCl$_3$) δ: 1.29 (3H, t, J=7.6 Hz), 2.76 (2H, q, J=7.6 Hz), 7.18-7.28 (2H, m), 7.40 (1H, d, J=5.4 Hz), 7.64 (1H, s), 7.78 (1H, d, J=8.3 Hz)

(3) Synthesis of (4-Bromonaphthalen-2-yl)-(5-ethylbenzo-[b]thiophen-2-yl)methanol In a nitrogen stream, an n-butyllithium hexane solution (1.6 M, 1.44 ml, 2.30 mmol) was added dropwise to a solution of 5-ethylbenzo[b]thiophene (373 mg, 2.30 mmol) in THF (15 ml) at −78° C., and the reaction solution was stirred at the same temperature for 5 minutes. To this mixture, a solution of 4-bromonaphthalene-2-carbaldehyde (515 mg, 2.19 mmol) in THF (5 ml) was added dropwise at −78° C., and the resulting mixture was stirred at the same temperature for two hours and at −20° C. for 30 minutes, and then a saturated ammonium chloride aqueous solution was added and the mixture was extracted with ethyl acetate. The organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:9)] to obtain the title compound (780 mg, 90%).

$^1$H-NMR (CDCl$_3$) δ: 1.24 (1H, t, J=7.6 Hz), 2.63 (1H, d, J=3.1 Hz), 2.73 (2H, q, J=7.6 Hz), 6.23 (1H, d, J=3.1 Hz), 7.14 (2H, s), 7.52-7.70 (4H, m), 7.83-7.93 (3H, m), 8.22 (1H, d, J=8.3 Hz)

(4) Synthesis of 2-(4-Bromonaphthalen-2-ylmethyl)-5-ethylbenzo[b]thiophene

In a nitrogen stream, triethylsilane (0.63 ml, 3.93 mmol) and a boron trifluoride-diethyl ether complex (0.27 ml, 2.16 mmol) were added to a solution of (4-bromo-naphthalen-2-yl)-(5-ethylbenzo[b]-thiophen-2-yl)methanol (780 mg, 1.96 mmol) in methylene chloride (20 ml) at 0° C. and the reaction mixture was stirred at room temperature for three hours. To the obtained solution was added methanol (10 ml) and water (30 ml) and the mixture was extracted with methylene chloride. The organic layer was washed with a saturated sodium chloride aqueous solution and dried (anhydrous magnesium sulfate), and then the solvent was distilled under reduced pressure. The obtained residue was purified by silica gel column chromatography [developing solution=n-hexane)] to obtain the title compound (460 mg, 62%).

$^1$H-NMR (CDCl$_3$) δ: 1.27 (1H, t, J=7.6 Hz), 2.73 (2H, q, J=7.6 Hz), 4.34 (2H, s), 7.10 (1H, s), 7.13 (1H, d, J=7.6 Hz), 7.48-7.79 (7H, m), 8.19 (1H, d, J=8.3 Hz)

(5) Synthesis of (3R,4R,5S,6R)-3,4,5-Trisbenzyloxy-6-benzyloxymethyl-2-[3-(5-ethylbenzo[b]thiophen-2-yl-methyl)naphthalen-1-yl]tetrahydropyran-2-ol In a nitrogen stream, an n-butyllithium hexane solution (1.6 M, 0.83 ml, 1.33 mmol) was added dropwise to a solution of 2-(4-bromonaphtalen-2-ylmethyl)-5-ethylbenzo-[b]thiophene (460 mg, 1.21 mmol) in THF (15 ml) at −78° C. The reaction mixture was stirred at the same temperature for five minutes and to this solution, a solution of 3,4,5-trisbenzyloxy-6-benzyloxymethyltetrahydro-pyran-2-one (844 mg, 1.57 mmol) in THF (5 ml) was added dropwise. The reaction solution was stirred at −78° C. for five minutes and a saturated ammonium chloride aqueous solution was added to stop the reaction. The reaction mixture was extracted with ethyl acetate and the organic layer was washed with a saturated sodium chloride aqueous solution and dried (anhydrous magnesium sulfate), and then the solvent was distilled under reduced pressure. The obtained residue was purified by silica gel column chromatography [developing solution=ethyl acetate:n-hexane (1:9)] to obtain the title compound (1.06 mg, 100%).

$^1$H-NMR (CDCl$_3$) δ: 1.25 (3H, t, J=7.6 Hz), 2.72 (2H, q, J=7.6 Hz), 4.35 (2H, s), 3.45-4.78 (12H, m), 4.89 (2H, s), 4.92-4.98 (1H, m), 6.67 (2H, d, J=7.2 Hz), 6.94 (2H, t, J=7.2 Hz), 7.01-7.44 (21H, m), 7.59 (1H, d, J=8.3 Hz), 7.75 (1H, s), 7.79 (1H, d, J=7.9 Hz), 7.89 (1H, d, J=1.7 Hz), 8.62 (1H, d, J=8.6 Hz)

(6) Synthesis of (3R,4R,5S,6R)-3,4,5-Trisbenzyloxy-2-benzyloxymethyl-6-[3-(5-ethylbenzo[b]thiophen-2-ylmethyl)naphthalen-1-yl]tetrahydropyran In a nitrogen stream, triethylsilane (0.60 ml, 3.78 mmol) and a boron trifluoride-diethyl ether complex (0.17 ml, 1.32 mmol) were added to a solution of (3R,4R,5S,6R)-3,4,5-trisbenzyloxy-6-benzyloxy-methyl-2-[3-(5-ethylbenzo-[b] thiophen-2-ylmethyl)-naphthalen-1-yl]tetrahydropyran-2-ol (1.06 g, 1.26 mmol) in methylene chloride (20 ml) at −40° C. The reaction mixture was stirred at 0° C. for one hour, and then a 50% methanol aqueous solution (20 ml) was added thereto. The resulting mixture was extracted with methylene chloride and the organic layer was washed with a saturated sodium chloride aqueous solution and dried with sodium sulfate. The solvent was distilled under reduced pressure and the obtained residue was purified by silica gel column chromatography [developing solution=ethyl acetate:n-hexane (1:9)] to obtain the title compound (670 mg, 65%).

$^1$H-NMR (CDCl$_3$) δ: 1.26 (3H, t, J=7.6 Hz), 2.71 (2H, q, J=7.6 Hz), 3.42 (1H, d, J=10.3 Hz), 3.60-4.00 (6H, m), 4.09 (1H, d, J=10.3 Hz), 4.35 (2H, s), 4.46-4.72 (3H, m), 4.82-4.98 (4H, m), 6.50 (2H, d, J=7.2 Hz), 6.85-7.85 (27H, m), 8.37 (1H, d, J=8.2 Hz)

(7) Synthesis of (2R,3S,4R,5R,6S)-2-Hydroxymethyl-6-[3-(5-ethylbenzo[b]thiophen-2-ylmethyl) naphthalen-1-yl]-tetrahydropyran-3,4,5-triol Under a nitrogen atmosphere, dimethylsulfide (2.66 ml) and a boron trifluoride-diethyl ether complex (1.03 ml, 8.12 mmol) were added to a solution of (3R,4R,5S,6R)-3,4,5-trisbenzyloxy-2-benzyloxymethyl-6-[3-(5-ethylbenzo[b]-thiophen-2-ylmethyl)naphthalen-1-yl]tetrahydropyran (670 mg, 0.81 mmol) in methylene chloride (4 ml) under cooling with ice. The reaction mixture was stirred at room temperature for 1.5 days, and then a 50% methanol aqueous solution (20 ml) was added under cooling with ice and the mixture was extracted with methylene chloride. The organic layer was washed with a saturated sodium chloride aqueous solution and dried with sodium sulfate, and then the solvent was distilled under reduced pressure. The obtained residue was purified by silica gel column chromatography [developing solution=methylene chloride:methanol (50:1)] to obtain the title compound (119 mg, 32%).

$^1$H-NMR (CD$_3$OD) δ: 1.26 (3H, t, J=7.6 Hz), 2.71 (2H, q, J=7.6 Hz), 3.45-3.65 (3H, m), 3.66-3.82 (2H, m), 3.89 (1H, d, J=12.1 Hz), 4.39 (2H, s), 4.90 (1H, d, J=9.6 Hz), 7.05-7.15 (2H, m), 7.40-7.55 (3H, m), 7.58-7.66 (2H, m), 7.37 (1H, s), 7.78-7.85 (1H, m), 8.24-8.32 (1H, m)

MS (ESI$^+$): 487 [M+Na]$^+$

The structures of the compounds of the above-described Examples will be shown in Table 1.

TABLE 1

| Compound 1 | 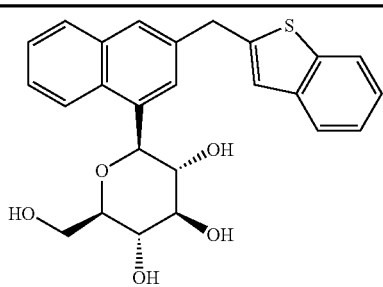 |
|---|---|
| Compound 2 | 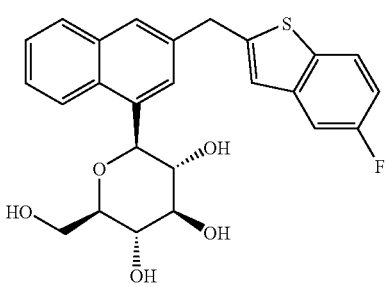 |

TABLE 1-continued

| Compound 3 | 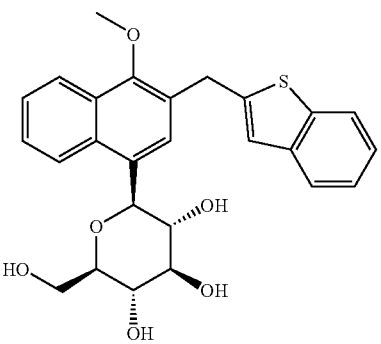 |
|---|---|
| Compound 4 | 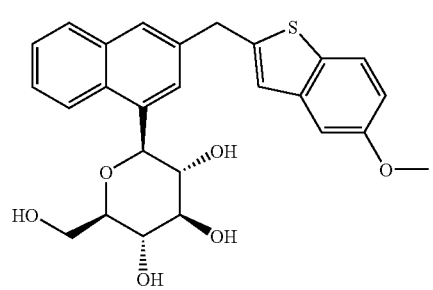 |
| Compound 5 | 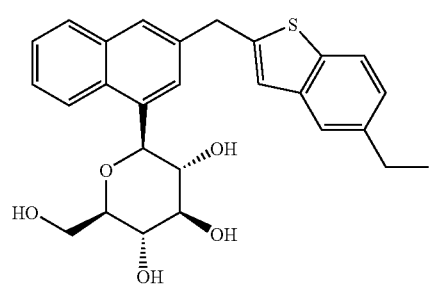 |

By operating the same procedure as in the above-described Examples, the compounds of the present invention as set forth in the Table below were prepared with the use of the corresponding starting materials and reagents.

TABLE 2

| Compound 6 | 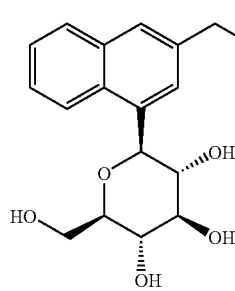 | $^1$H-NMR (CD$_3$OD) δ: 3.50-3.63 (3H, m), 3.69-3.80 (2H, m), 3.99 (1H, dd, J=11.7, 1.9 Hz), 4.40 (2H, s), 4.90 (1H, d, J=9.6 Hz), 7.09 (1H, s), 7.21 (1H, dd, J=8.6, 2.0 Hz), 7.42-7.51 (2H, m), 7.62-7.74 (4H, m), 7.79-7.83 (1H, m), 8.28 (1H, m) MS (ESI$^+$): 493 [M+Na]$^+$ |
|---|---|---|

TABLE 2-continued

| Compound 7 | 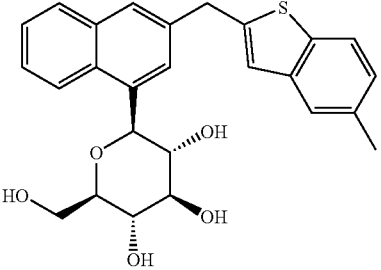 | ¹H-NMR (CD₃OD) δ: 2.37 (3H, s), 2.56 (1H, br s), 3.45 (1H, m), 3.54-3.90 (5H, m), 4.40 (2H, s), 4.81 (1H, d, J=9.2 Hz), 6.89 (1H, s), 7.02 (1H, dd, J=8.4, 1.5 Hz), 7.35-7.45 (3H, m), 7.48 (1H, s), 7.54 (1H, d, J=8.4 Hz), 7.65 (1H, s), 7.71-7.78 (1H, m), 8.11 (1H, m) MS (ESI⁺): 473 [M+Na]⁺ |
|---|---|---|
| Compound 8 | 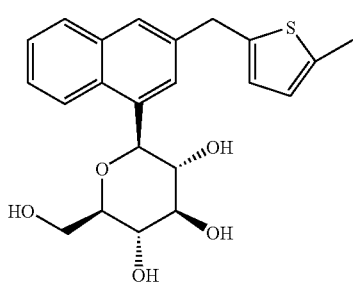 | ¹H-NMR (CD₃OD) δ: 2.38 (3H, s), 3.51-3.63 (3H, m), 3.69-3.81 (2H, m), 3.90 (1H, d, J=12, 1 Hz), 4.22 (2H, s), 4.88 (1H, d, J=9.6 Hz), 6.56 (1H, d, J=3.4 Hz), 6.63 (1H, d, J=3.4 Hz), 7.39-7.48 (2H, m), 7.57 (1H, s), 7.64 (1H, s), 7.78 (1H, d, J=9.5 Hz), 8.25 (1H, d, J=9.5 Hz) MS (ESI⁺): 423 [M+Na]⁺ |
| Compound 9 | 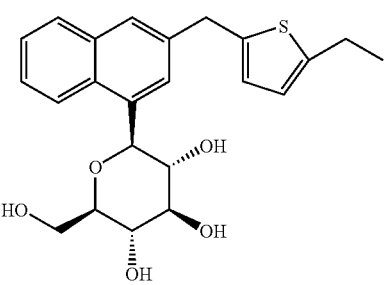 | ¹H-NMR (CD₃OD) δ: 1.23 (3H, t, J=7.5 Hz), 2.75 (2H, q, J=7.5 Hz), 3.51-3.63 (3H, m), 3.69-3.81 (2H, m), 3.89 (1H, d, J=12.0 Hz), 4.23 (2H, s), 4.89 (1H, d, J=9.0 Hz), 6.56 (1H, s), 6.65 (1H, s), 7.42-7.45 (2H, m), 7.57 (1H, s), 7.65 (1H, s), 7.78 (1H, d, J=8.4 Hz), 8.25 (1H, d, J=9.0 Hz) MS (ESI⁻): 413 [M−1]⁻ |

Experimental Example 1

Test for Confirming Action of Inhibiting Human Na⁺-Glucose Co-Transporters (SGLT1 and SGLT2)

(1) Preparation of Human SGLT1 Expression Vector

PCR was performed by KOD+DNA polymerase (a product of Toyobo Co., Ltd.) by taking a human small intestine-derived cDNA library (a product of Clontech) as a template with the use of a synthesized DNA primer to amplify human SGLT1 cDNA. Then, the amplified fragment was cloned to pcRII-Topo vector with the use of a Topo TA Cloning Dual Promoter kit (a product of Invitrogen) and introduced into *E. coli* competent cells (TOP10, a product of Invitrogen), and clones which exhibited resistance to ampicillin were proliferated in an LB medium containing ampicillin (50 mg/L). From the proliferated *E. coli*, a plasmid was purified according to the usual way (see Maniatis et al., *Molecular Cloning*). By taking this plasmid as a template, PCR was performed by KOD+DNA polymerase with the use of a synthetic DNA primer into which restriction enzyme recognition sites had been introduced to amplify human SGLT1 cDNA (a fragment added with an Eco RI recognition site on the upstream side and a Hind III recognition site on the downstream side). This amplified fragment was subjected to Eco RI and Hind III digestion to connect the digested fragments to their recognition sites of expression vector pcDNA 3.1(−) (a product of Invitrogen) with the use of a Rapid DNA Ligation kit (a product of Roche Diagnostics). The connected expression vector was introduced into *E. coli* competent cells (DH5α, a product of Invitrogen) and proliferated in an ampicillin-containing LB medium to obtain a human SGLT1 expression vector according to the usual way.

(2) Preparation of Human SGLT2 Expression Vector

PCR was performed by KOD+DNA polymerase by taking a human kidney-derived cDNA library (a product of Clontech) as a template with the use of a synthesized DNA primer to amplify human SGLT2 cDNA. Then, the amplified fragment was cloned to pcRII-Topo vector with the use of the Topo TA Cloning Dual Promoter kit and then introduced into *E. coli* competent cells (TOP10), and clones which exhibited resistance to ampicillin were proliferated in an LB medium containing ampicillin (50 mg/L). From the proliferated *E. coli*, a plasmid was purified according to the usual way. By taking this plasmid as a template, PCR was performed by KOD+DNA polymerase with the use of a synthetic DNA primer into which restriction enzyme recognition sites had been introduced to amplify human SGLT2 cDNA (a fragment added with Xho I recognition site on the upstream side and a Hind III recognition site on the downstream side). This amplified fragment was subjected to Xho I and Hind III digestion to connect the digested fragments to their recognition sites of the expression vector pcDNA 3.1(−) with the use of the Rapid DNA Ligation kit. The connected expression vector was introduced into *E. coli* competent cells (DH5α) and proliferated in an ampicillin-containing LB medium to obtain a human SGLT2 expression vector according to the usual way.

(3) Preparation of Human SGLT1 Stable Expression Cell and Human SGLT2 Stable Expression Cell The human SGLT1 expression vector or the human SGLT2 expression vector which was digested with restriction enzyme Pvu I was introduced into CHO-K1 cells with the use of FuGene (a product of Roche Diagnostics). After introduction of the gene, the cells were incubated in a DMEM medium (a product of Gibco) containing penicillin (50 U/mL, a product of Sigma), streptomycin (50 mg/L, a product of Sigma), Geneticin (200 mg/L, a product of Nacalai Tesque) and 20% bovine fetal serum in the presence of 5% $CO_2$ at 37° C. for about three weeks to obtain Genticin-resistant clones. From these clones, cells capable of stably expressing human SGLT1 or the human SGLT2 were selected and obtained by using sodium dependent sugar (methyl-α-D-glucopyranoside) intake activity as an index.

(4) Determination of Activity of Inhibiting Methyl-α-D-glucopyranoside Intake

The human SGLT1 stable expression CHO cells or the human SGLT2 stable expression CHO cells was seeded in a 96-well plate to a density of 30,000 to 40,000 cells/well and incubated for four to six days. Next, the medium of the culture plate was removed, and a pretreatment buffer (a buffer containing 140 mM of choline chloride, 2 mM of potassium chloride, 1 mm of calcium chloride, 1 mM of magnesium chloride, 10 mM of 2-[4-(2-hydroxyethyl)-1-piperazinyl] ethanesulfonic acid and tris(hydroxymethyl)-aminomethane and having a pH of 7.4) was added in an amount of 150 μL per well and then left to stand at 37° C. for 20 minutes. The pretreatment buffer was removed and the pretreatment buffer was again added in an amount of 50 μL per well and then left to stand at 37° C. for 20 minutes. To 100 mL of a buffer (a buffer containing 140 mM of sodium chloride, 2 mM of potassium chloride, 1 mM of calcium chloride, 1 mM of magnesium chloride, 1 mM of methyl-α-D-glucopyranoside, 10 mM of [4-(2-hydroxyethyl)-1-piperazinyl]ethanesulfonic acid and tris(hydroxymethyl)-aminomethane and having a pH of 7.4), there was added and mixed 6.3 mL of methyl-α-D-(U-$^{14}$C)glucopyranoside (200 mCi/L, a product of Amersham Pharmacia Biotech) to prepare an intake buffer, and a test compound was dissolved in this intake buffer and the resulting solution was used as a buffer for determining inhibition activity. Further, as a control, a test compound-free intake buffer was used. Furthermore, in order to determine a basic intake in the absence of the test compound and sodium, a basic intake buffer containing 140 mM of choline chloride instead of the sodium chloride was prepared in the same manner and used in the determination. The pretreatment buffer was removed from the wells of the culture plate and a buffer for determining inhibition activity was added in an amount of 35 μL per well and was left to stand at 37° C. for 45 minutes. Then, the buffer for determining inhibition activity was removed and a washing buffer (a buffer solution containing 140 mM of choline chloride, 2 mM of potassium chloride, 1 mM of calcium chloride, 1 mM of magnesium chloride, 10 mM of methyl-α-D-glucopyranoside, 10 mM of 2-[4-(2-hydroxy-ethyl)-1-piperazinyl]ethane-sulfonic acid and tris(hydroxymethyl)aminomethane and having a pH of 7.4) was added in an amount of 300 μL per well and immediately removed. This washing operation was repeated again, and a cell solubilizing solution (1 M of sodium hydroxide and 0.1% of sodium lauryl sulfate) was added in an amount of 30 μL per well to solubilize cells. Thereto was added 15 μL of 2 M hydrochloric acid, and 40 μL of the obtained solution was transferred to a Luma-plate (a product of Packard) and was left to stand at room temperature overnight to evaporate the solvent. The radioactivity of the sample on the plate was determined on a Topcount (manufactured by Packard). The test compound concentration ($IC_{50}$ value) which inhibited 50% of intake, when the value obtained by deducting a basic intake from the intake of the control was taken as 100%, was calculated from the concentration-inhibition curve by using an arithmetic software (ELfit ver. 3). As a result, the compounds of the present invention exhibited remarkable SGLT2 inhibition action. The $IC_{50}$ values for the SGLT2 inhibition of the representative compounds of the present invention are shown in Table 3.

TABLE 3

| Test Compound | $IC_{50}$ (nM) |
|---|---|
| Example 1 | 18 |
| Example 8 | 18 |

Experimental Example 2

Test for Determining Blood Half-Life in Rat

A test compound was intravenously administered to a SD male rat (8-weeks old, Japan SLC) and the blood was collected 2 minutes, 5 minutes, 15 minutes, 30 minutes, 1 hour, 2 hours, 4 hours, 6 hours and 8 hours after administration, respectively. The obtained blood was centrifuged to obtain plasma. The plasma sample (0.01 mL) and water (0.4 mL) were added to a tube added with an internal standard substance of phenyloin (250 ng), and diethyl ether (2 mL) was added thereto and the obtained solution was stirred for five minutes, and then centrifuged for 10 minutes and an organic layer was recovered and subjected to nitrogen dryness, and a mobile phase was added to the obtained solid to dissolve it and the resulting solution was taken as a sample for determination.

The sample for determination was injected into LC-MS/MS and determined under the following conditions.

Column: ODS (2.0×150 mm)

Mobile Phase Acetonitrile/10 mM ammonium acetate=4/6 (v/v)

Flow Rate: 0.2 mL/min

Amount of Sample Injected: 10 μL

Mass Analysis: ESI (+)

The plasma concentration obtained by the LC-MS/MS method was subjected to non-compartmental analysis with the use of the WinNonlin standard made by Pharsight Corporation to calculate pharmacokinetic parameters. The half-life in the final layer is as shown in Table 4.

TABLE 4

| (Dosage: 10 mg/kg) | |
|---|---|
| Test Compound | Half-Life (hr) |
| Example 1 | 8.21 |

INDUSTRIAL APPLICABILITY

By the present invention there are provided glucitol compounds which exhibit excellent action of inhibiting SGLT2 activity, their prodrugs or their pharmaceutically acceptable salts. Further, the compounds of the present invention are useful as prophylactic or therapeutic agents for diabetes, diabetes-related diseases or diabetic complications.

The invention claimed is:
1. A compound represented by formula (IA):

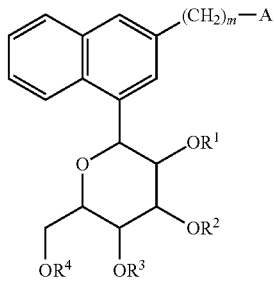

wherein
m is an integer selected from 1 to 3;
$R^1$, $R^2$, $R^3$ and $R^4$ are each independently selected from a hydrogen atom, a $C_1$-$C_6$ alkyl group which may be substituted with one or more Ra, a $C_7$-$C_{14}$ aralkyl group which may be substituted with one or more Rb, and —C(=O)Rx;
Rx is a $C_1$-$C_6$ alkyl group which may be substituted with one or more Ra, an aryl group which may be substituted with one or more Rb, a heteroaryl group which may be substituted with one or more Rb, a $C_1$-$C_6$ alkoxy group which may be substituted with one or more Ra, or —NReRf;
A is a heteroaryl group selected from a thienyl group and a benzothienyl group which may be substituted with one or more Rb, provided that when A is a benzothienyl group, the group —$(CH_2)_m$— is linked on to a thiophene in A;
Ra is each independently selected from a halogen atom, a hydroxy group, a cyano group, a nitro group, a carboxyl group, a $C_1$-$C_6$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_1$-$C_6$ alkylthio group which may be substituted with one or more Rc, a $C_1$-$C_6$ alkylsulfinyl group which may be substituted with one or more Rc, a $C_1$-$C_6$ alkylsulfonyl group which may be substituted with one or more Rc, —NRfRg, a $C_1$-$C_6$ alkoxycarbonyl group which may be substituted with one or more Rc, and a $C_1$-$C_6$ alkylcarbonyl group which may be substituted with one or more Rc;
Rb is each independently selected from a $C_1$-$C_6$ alkyl group which may be substituted with one or more Rc, a halogen atom, a $C_1$-$C_6$ alkoxy group which may be substituted with one or more Rc;
Rc is each independently selected from a halogen atom, a hydroxy group, a cyano group, a nitro group, a carboxyl group, a $C_1$-$C_6$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_1$-$C_6$ alkylamino group, and a di($C_1$-$C_6$ alkyl)amino group;
Rd is each independently selected from a $C_1$-$C_6$ alkyl group which may be substituted with one or more halogen atoms, a $C_7$-$C_{14}$ aralkyl group, a halogen atom, a hydroxy group, a cyano group, a nitro group, an amino group, a $C_1$-$C_6$ alkylamino group, and a di($C_1$-$C_6$alkyl) amino group;
Re is a hydrogen atom, a $C_1$-$C_6$ alkyl group which may be substituted with one or more Rc, an aryl group which may be substituted with one or more Rd, or a heteroaryl group which may be substituted with one or more Rd;
Rf is a hydrogen atom, or a $C_1$-$C_6$ alkyl group which may be substituted with one or more Rc;
Rg is a hydrogen atom, a $C_1$-$C_6$ alkyl group which may be substituted with Rc, a $C_1$-$C_6$ alkylcarbonyl group which may be substituted with one or more Rc, an aryl group which may be substituted with Rd, a heteroaryl group which may be substituted with one or more Rd, a carbamoyl group, a $C_1$-$C_6$ alkoxycarbonyl group which may be substituted with one or more Rc, or a $C_1$-$C_6$ alkylsulfonyl group which may be substituted with one or more Rc; or
Re and Rf, and Rf and Rg may form a 4- to 7-membered heterocycle together with the nitrogen atom to which they are bonded;
or a prodrug or a pharmaceutically acceptable salt thereof.

2. A compound according to claim 1 represented by formula (Ic):

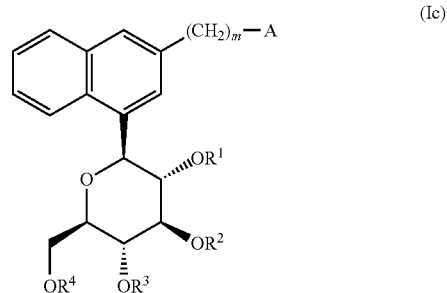

wherein A, $R^1$, $R^2$, $R^3$, $R^4$ and m are the same as defined in claim 1,
or a prodrug or a pharmaceutically acceptable salt thereof.

3. A compound according to claim 1, wherein m is 1, or a prodrug or a pharmaceutically acceptable salt thereof.

4. A compound according to claim 1, wherein $R^1$, $R^2$, $R^3$ and $R^4$ are each independently selected from a hydrogen atom and —C(=O)Rx, and Rx is a $C_1$-$C_6$ alkyl group which may be substituted with one or more Ra, or a $C_1$-$C_6$ alkoxy group which may be substituted with one or more Ra, or a prodrug or a pharmaceutically acceptable salt thereof.

5. A compound selected from the group consisting of:
(2S,3R,4R,5S,6R)-2-[3-(benzo[b]thiophen-2-ylmethyl) naphthalen-1-yl]-6-hydroxymethyl-tetrahydropyran-3, 4,5-triol;
(2S,3R,4R,5S,6R)-2-[3-(5-fluorobenzo[b]thiophen-2-yl-methyl)naphthalen-1-yl]-6-hydroxymethyl-tetrahydro-pyran-3,4,5-triol;
(2R,3S,4R,5R,6S)-2-hydroxymethyl-6-[3-(5-methoxy-benzo[b]-thiophen-2-ylmethyl)naphthalen-1-yl]tet-rahydropyran-3,4,5-triol;
(2S,3R,4R,5S,6R)-2-[3-(5-ethylbenzo[b]thiophen-2-yl-methyl)naphthalen-1-yl]-6-hydroxymethyl-tetrahydro-pyran-3,4,5-triol;
(2S,3R,4R,5S,6R)-2-[3-(5-chlorobenzo[b]thiophen-2-yl-methyl)naphthalen-1-yl]-6-hydroxymethyl-tetrahydro-pyran-3,4,5-triol;

(2R,3S,4R,5R,6S)-2-hydroxymethyl-6-[3-(5-methyl-benzo[b]-thiophen-2-ylmethyl)naphthalen-1-yl]tetrahydropyran-3,4,5-triol;

(2R,3S,4R,5R,6S)-2-hydroxymethyl-6-[3-(5-methylthiophen-2-ylmethyl)naphthalen-1-yl]tetrahydropyran-3,4,5-triol; and (2R,3S,4R,5R,6S)-2-hydroxymethyl-6-[3-(5-ethylthiophen-2-ylmethyl)naphthalen-1-yl]tetrahydropyran-3,4,5-triol, or a prodrug or a pharmaceutically acceptable salt thereof.

6. A pharmaceutical composition comprising a compound according to claim 1 or a prodrug or a pharmaceutically acceptable salt thereof, which is used as a Na$^+$-glucose co-transporter inhibitor.

7. A pharmaceutical composition comprising a compound according to claim 1 or a prodrug or a pharmaceutically acceptable salt thereof, which is used for prophylaxis or therapy of insulin-independent diabetes (type II diabetes), diabetic complications caused by hyperglycemia, or obesity.

8. A method of preventing or treating insulin-independent diabetes (type II diabetes), diabetic complications caused by hyperglycemia, or obesity, which comprises administering an effective therapeutic amount of a compound according to claim 1 or a prodrug or a pharmaceutically acceptable salt thereof to a patient in need thereof.

9. A pharmaceutical composition comprising a compound according to claim 1 or a prodrug or a pharmaceutically acceptable salt thereof, which is used for therapy of diabetes, diabetic complications caused by hyperglycemia, or obesity.

10. A method of treating diabetes, diabetic complications caused by hyperglycemia, or obesity, which comprises administering an effective therapeutic amount of a compound according to claim 1 or a prodrug or a pharmaceutically acceptable salt thereof to a patient in need thereof.

* * * * *